United States Patent [19]

Nakai et al.

[11] Patent Number: 5,837,230

[45] Date of Patent: Nov. 17, 1998

[54] METHODS OF TREATING ALLERGIES WITH M-CSF

[75] Inventors: Satoru Nakai, Itano-gun; Masayuki Takahashi, Naruto; Hiroyuki Ichikawa, Tokushima; Yoshikatsu Hirai, Itano-gun, all of Japan

[73] Assignee: Otsuka Pharmaceutical Co., Ltd., Japan

[21] Appl. No.: 464,463

[22] Filed: Jun. 5, 1995

Related U.S. Application Data

[63] Continuation of Ser. No. 730,882, Sep. 13, 1991, abandoned, which is a continuation-in-part of Ser. No. 517,752, May 2, 1990, abandoned.

[30] Foreign Application Priority Data

Dec. 13, 1989 [JP] Japan ......................................... 323518
Dec. 12, 1990 [WO] WIPO ........................ PCT/JP90/01629

[51] Int. Cl.[6] .................................................. A61K 38/19
[52] U.S. Cl. ................................. 424/85.1; 514/2; 514/8; 514/12; 514/885
[58] Field of Search ............................... 424/85.1; 514/2, 514/8, 12, 885

[56] References Cited

U.S. PATENT DOCUMENTS

| | | |
|---|---|---|
| 4,745,115 | 5/1988 | Bender et al. . |
| 4,752,578 | 6/1988 | Moore et al. . |
| 4,772,685 | 9/1988 | Schmidt et al. . |
| 4,778,806 | 10/1988 | Bender et al. . |
| 4,780,470 | 10/1988 | Bender et al. . |
| 4,782,014 | 11/1988 | Serban et al. . |
| 4,794,114 | 12/1988 | Bender et al. . |
| 4,868,119 | 9/1989 | Clark et al. . |
| 4,870,101 | 9/1989 | Ku et al. . |
| 4,870,174 | 9/1989 | Paradies . |
| 4,882,435 | 11/1989 | Paradies . |
| 4,894,454 | 1/1990 | Paradies . |
| 4,897,397 | 1/1990 | Shih et al. . |
| 4,912,136 | 3/1990 | Wood . |
| 5,104,650 | 4/1992 | Ralph et al. ........................ 424/85.1 |
| 5,171,625 | 12/1992 | Cerrutti et al. ........................ 435/69.1 |

FOREIGN PATENT DOCUMENTS

| | | |
|---|---|---|
| 0 261 592 | 3/1988 | European Pat. Off. . |
| 0276551 | 3/1988 | European Pat. Off. . |
| 0272729 | 6/1988 | European Pat. Off. . |
| 0331088 | 9/1989 | European Pat. Off. . |
| 1-221324 | 9/1989 | Japan . |
| WO 89/01946 | 3/1989 | WIPO . |
| WO 89/02746 | 4/1989 | WIPO . |
| WO 89/04664 | 6/1989 | WIPO . |
| WO 89/09060 | 10/1989 | WIPO . |

OTHER PUBLICATIONS

Borish et al *Clin Allergy* 76(4) 1992, pp. 785–787.
Duma et al *J. Immunol* 141(9) 1988, pp. 3186–3189.
Wong et al *Science* 235, 1987, pp. 1504–1509.
J.W. Larrick, Immunol. Today 10:61–66 (1989).
C.H. Hannum et al., Nature 343:336–340 (1990).
S.P. Eisenberg et al., Nature 343:341–346 (1990).
J.W. Larrick and S.L. Kunkel, Pharma. Resh. 5:129–139 (1988).
C.P.J. Maury, Acta Med. Scand. 220:291–294 (1986).
M. Takahashi et al., B.B.R.C. 161:892–901 (1989).
I. Nakoinz et al., Exp. Hematol. 17: 699 (1989).
J.J. Oppenheim etal., Immunol. Today 7:45–56 (1986).
M. Takahashi et al., B.B.R.C. 152:1401–1409 (1988).
C.A. Dinarello, in Inflammation: Basic Principles and Clinical Correlates, pp. 195–208, eds. J.I. Gallin et al. Ravin Press N.Y. (1988).
Wing et al., The Journal of Immunology, vol. 137, No. 9, pp. 2768–2773, Nov. 1, 1986.
Strassman et al., The Journal of Immunology, vol. 147, No. 4, pp. 1279–1285, Aug. 15, 1991.

*Primary Examiner*—John Ulm
*Assistant Examiner*—Prema Mertz
*Attorney, Agent, or Firm*—Finnegan, Henderson, Farabow, Garrett & Dunner

[57] ABSTRACT

This invention provides medical uses of a M-CSF, particularly a method and composition for treating inflammatory disease and allergy using natural M-CSF or recombinant M-CSF or the derivatives thereof.

8 Claims, 10 Drawing Sheets

1/DILUTION OF CONDITIONED MEDIUM
ADDED TO CON A THYMOCYTES

C - Control

L - Lps (1 ug/ml)

M - Ec-80-I (1 ug/ml)

Con A IL-1 added to thymocytes

C - Control

L - Lps

M - MCSF (MF-1 Program)

* Radioreceptor Binding (% Displacement)
△--△ Inhibition of Thymocytes Stimulated with ConA and 0.03 ng/ml IL-1 Beta (%)

METHODS OF TREATING ALLERGIES WITH M-CSF

This application is a continuation of application Ser. No. 07/730,882, filed Sep. 13, 1991, now abandoned; which was a continuation-in-part of application Ser. No. 07/517,752, abandoned.

TECHNICAL FIELD

This invention relates to a method and a composition for treating inflammatory disease and allergy.

More particularly, the present invention relates to a method of treating a patient with inflammatory disease comprising administering an amount of macrophage-colony stimulating factor (hereinafter "M-CSF") effective to inhibit interleukin 1 (hereinafter "IL-1") biological activity and reduce symptoms of inflammatory disease. The present invention relates to a method of treating a patient with inflammatory disease comprising administering an amount of M-CSF that is effective to cause the production of an inhibitor of IL-1. The present invention also relates to a method for inhibiting IL-1 biological activity comprising administering a pharmaceutically effective amount of M-CSF.

This invention relates to a method of treating allergic disease comprising administering a pharmaceutically effective amount of M-CSF.

Further, the present invention relates to a novel anti-inflammatory agent and anti-allergic agent, and more particularly, to an anti-inflammatory agent and anti-allergic agent containing M-CSF as an active ingredient.

BACKGROUND ART

Inflammation is a complex of sequential changes in body tissues in response to injury caused by any number of agents such as bacteria, trauma, chemicals, or heat. Although the inflammatory response is a mechanism of resistance by the body in the presence of such agents, the inflammatory response has caused much pain in the many patients suffering from inflammatory diseases such as rheumatoid arthritis and gout.

The inflammatory response varies according to tissue involved, causative agent, etc., but there are several features that characterize the response. These include fenestration of the microvasculature, leakage of the elements of blood into the interstitial spaces and migration of leukocytes into the inflamed tissue. This is usually accompanied by clinical signs of erythema, edema, tenderness (called hyperalgesia), and pain. This complex response also involved the release and action of chemical mediators such as histamine, 5-hydroxytryptamine (5-HT), slow, reacting substance of anaphylaxis (SRS-A), various chemotactic factors, bradykinin, and prostoglandins. In addition, phagocytic cells migrate into the area, causing the rupture of cellular lysosomal membranes and the release of lytic enzymes. All these events may contribute to the inflammatory response.

The mechanism of action for the inflammatory response has been the focus of interest since the earliest days of medicine. The bark of willow and other plants had been used as a medicinal agent in many cultures for centuries. It has been reported that, in the mid-eighteenth century, the Reverend Edmund Stone described the success of the bark of the willow in the cure of "agues", i.e., fever. In 1827, Laroux discovered that the active ingredient in willow bark is salin, which led eventually to the production of salicyclic acid.

The success of salicylic acid and aspirin-like drugs in alleviating many of the symptoms of the inflammatory response is well known. These drugs, however, are not without serious side effects and disadvantages. For example, aspirin-like drugs inhibit or interfere with a variety of other enzymes and cellular systems. In addition, for the treatment of inflammatory diseases involving musculoskeletal disorders such as rheumatoid arthritis, osteoarthritis, and ankylosine soondilitis, aspirin-like drugs provide only symptomatic relief from the pain and inflammation associated with the disease and do not arrest the progression of pathological injury to tissue. Some practitioners believe that the drugs may aggravate the disease by allowing movement of arthritic joints that is not otherwise possible, which further promotes injury.

Aspirin-like drugs tend to induce gastric or intestinal ulceration that can sometimes be accompanied by secondary anemia from the resultant blood loss.

Other drugs previously used in the treatment of inflammatory diseases have equally serious side effects. For example, phenylbutazone, a pyrazolon derivative, was introduced in 1949 for the treatment of rheumatoid arthritis and related disorders. Although it is an effective anti-inflammatory agent, it presents serious toxicity problems with long-term use. Phenylbutazone is poorly tolerated by many patients who often report of nausea, vomiting, epigastric discomfort and skin rashes. Diarrhea, vertigo, insomnia, euphoria, nervousness, hematuria, and blurred vision have also been reported. More serious effects include peptic ulcers with hemorrhage or perforation, hypersensitivity reactions, ulceration stomatizis, hepatitis, nephritis, aplastic anemia, leukopenia, and agranulocytosis. In addition, a number of deaths have occurred, especially from aplastic anemia and agranulocytosis. Finally, because the toxic effects of the drug are more severe in elderly persons, it is not advisable to treat the elderly with this drug.

Indomethacin, the product of a laboratory search for drugs with anti-inflammatory properties, was introduced in 1963 for the treatment of rheumatoid arthritis and related disorders such as acute gout. It is effective and widely used but toxicity often limits its use. It has been reported that a very high percentage of patients (35 to 50%) experience untoward symptoms and about 20% must discontinue use. Gastrointestinal complaints include anorexia, nausea, and abdominal pain. Central nervous system effects include severe frontal headache, dizziness, vertigo, light-headedness, and mental confusion.

The aspirin-like drugs above are generally used, along with rest and physical therapy, for the treatment of inflammatory diseases such as rheumatoid arthritis. If the disease progresses despite this treatment, patients are generally next treated with gold or glucocorticoids.

The toxic effects of gold, ranging from about 25 to 50% of patients with serious toxicity in about 10%, primarily involve the skin and mucous membranes. Lesions of the mucous membranes include stomatitis, gastritis, colitis, and vaginitis. Severe blood dyscrasias may results from autotherapy. Thrombocytopenia occasionally occurs and accounts for many of the fatalities. Leukopenia, agranulocytosis, and aplastic anemia may also occur.

Glucocorticoids, cortisol and the synthetic analogs of cortisol, are also used in the treatment of inflammatory diseases, such as rheumatoid arthritis, because they have the ability to prevent or suppress the development of local heat, redness, swelling and tenderness by which inflammation is recognized. Moreover, corticosteroids inhibit the inflammatory response whether the inciting agent is radiant, mechanical, chemical, infectious, or immunological. Corticosteroids, however, merely suppress the inflammatory response and do so in such a manner that the drugs may mask the progression of the disease. Just as importantly, corticosteroid therapy, once started, may have to be continued for many years or for life.

Immunosuppressive agents, developed in the search for chemotherapeutic agents for neoplastic diseases, have been explored for use in inflammatory diseases such as systemic lupus erythematosus, necrotizing vasculitis, scleroderma, and rheumatoid arthritis. One such agent, cyclophosphamide, has been the subject of a number or investigations, but it should only be used with caution. In addition to its acute toxic effects as a nitrogen mustard, it also has a high potential for inducing sterility, teratogenic effects, mutations, and cancer.

Despite the availability of the anti-inflammatory agents above, scientists have continued to study the etiology of inflammatory diseases in an attempt to find additional and better treatments for inflammatory diseases. One very important recent finding is that the host response to injury and infection involves the production of interleukin 1 (hereinafter "IL-1"). IL-1 is a polypeptide immunoregulatory cytokine produced primarily by mononuclear phagocytes that has a profound effect in the body. IL-1 mediates tissue remodeling, repair and inflammation by helping to coordinate the activities of cells such as endothelial cells, granulocytes, osteoclasts, chondrocytes, fibroblasts, hematopoietic cells, nerve cells, and lymphoid cells. See J. W. Larrick, "Native interleukin 1 inhibitors", Reviews in *Immunology Today* 10: 61–66 (1989). The biological activities of IL-1 include the activation of T helper cells, induction of fever, stimulation of prostoglandin or collagenase production, neutrophil chemotaxis, induction of acute phase proteins and the suppression of plasma iron levels. See U.S. Pat. No. 4,794,114 to Bender, R. E. et al., "Inhibition of interleukin-1 production by monocytes and/or macrophages", issued Dec. 27, 1988.

Recent studies have implicated excessive or unregulated IL-1 production in exacerbating and/or causing diseases such as rheumatoid arthritis, osteoarthritis, toxic shock syndrome, Reiter's syndrome, gout, acute synovitis, and other acute or chronic inflammatory diseases such as the inflammatory reaction induced by endotoxin. See U.S. Pat. No. 4,794,114 to Bender, R. E. et al., "Inhibition of interleukin-1 production by monocytes and/or macrophages", issued Dec. 27, 1988.

Accordingly, researchers in the field have considered treating inflammatory disease with inhibitors of IL-1. The mechanism of IL-1 inhibition varies and includes limiting IL-1 transcription, interfering with IL-1 binding by binding directly to the IL-1 receptor, and acting at other sites to limit the activity of the IL-1 receptor.

A recent review by J. W. Larrick, entitled "Native interleukin 1 inhibitors", in *Immunology Today* 10: 61–66 (1989) discussed IL-1 inhibitors including urine-derived inhibitors (see also PCT patent application WO 89/01946, PCT No.PCT/US88/02819, to Dayer et al. published Mar. 9, 1989), uromodulin, monocyte-macrophage derived inhibitors (see also Hannum, C. H., et al., "Interleukin-1 receptor antagonist activity of a human interleukin-1 inhibitor," *Nature* 343: 336–3340 (Jan. 25, 1990); Eisenberg, S. P. et al., "Primary structure and functional expression from complementary DNA of a human interleukin-1 receptor antagonist," *Nature* 343: 341–346 (Jan. 25, 1990)), and virus-infected macrophages. A more recent article has suggested that none of these inhibitors has been purified and characterized. Hannum, C. H., et al., "Interleukin-1 receptor antagonist activity of a human interleukin-1 inhibitor," *Nature* 343: 336–3340 (Jan. 25, 1990).

Nonnative inhibitors of IL-1 have also been discussed. See, for example, U.S. Pat. No. 4,870,101 to G. Ku, entitled "Method of inhibiting interleukin-1 release", issued Sep. 26, 1989 (providing compounds with antioxidant properties) and U.S. Pat. No. 4,780,470 to Bender et al., entitled "Inhibition of interleukin-1 by monocytes and/or macrophages," issued Oct. 25, 1988 (relating to the use of a 4,5-diaryl-2(substituted-imidazole), U.S. Pat. No. 4,778, 806, to Bender et al., entitled "Inhibition of interleukin-1 production by monocytes and/or macrophages," issued Oct. 18, 1988 (relating to the use of 2-2'[1,3-propan-2-onediyl-bis(thio)]bis-1H-imadazole), U.S. Pat. No. 4,794,114 to Bender et al., entitled "Inhibition of interleukin-1 production by monocytes and/or macrophages," issued Dec. 27, 1988 (relating to the use of a diaryl-substituted imidazole fused to a thiazole pyrrolidine, thiazide or piperidine ring).

Despite the number of IL-1 inhibitors available, it is believed that only glucocorticoids inhibit IL-1 at transcriptional and post-transcriptional levels. As discussed above, glucocorticoids present serious side effects especially if implicated for long term therapy.

Thus, there is a need in the art for inhibitors of IL-1 that could be used in the treatment of inflammatory diseases. The need could be best met by an inhibitor of IL-1 that has been studied for its beneficial effects in the treatment of other diseases. The side effects and any possible toxicology as well as tolerance levels would be known for such an inhibitor.

One of the agents of recent interest is macrophage colony-stimulating factor, one of the colony stimulating factors that function as a hematopoietic growth factor. This agent is promising because it has been found to be useful in the treatment of a variety of diseases. For example, M-CSF is able to promote the function of leukocytes and is therefore effective as a drug for preventing and curing various infectious diseases (Lopez, A. F. et al., *J. Immunol.*, 131: 2983 (1983); Handam, E. et al., *J. Immunol.*, 122:1134 (1979); and Vadas, M. A. et al., *J. Immunol.*, 130: 795 (1983)). In addition, M-CSF has been found to be effective for curing myelogenous leukemia because of its differentiation inducing activity (Metcalf, D. et al., *Int. J. Cancer*, 30: 773 (1982)). M-CSF is also thought to alleviate the leukopenia resulting from cancer chemotherapy and radiotherapy (European Patent Publication 261592).

The use of M-CSF in the treatment of inflammatory diseases, however, could be surprising because earlier reports had suggested that the growth factor M-CSF would promote IL-1 production, rather than inhibit it. For example, Moore, R. N., et al. "Procedure of Lymphocyte Activating Factor [Interleukin 1] by Macrophages activated with colony stimulating factors, "Journal of Immunology, 125: 1302 (1980) and Kurland, J. I., et al. "Induction of Prostaglandin E Synthesis in Normal and Neoplastic Macrophages; Role of Colony Stimulating Factors Distinct from Effects on Myeloid Progenitor Cell Proliferation, "Proceedings of the National Academy of Sciences 76: 2326 (1979), discuss the production of IL-1 and prostoglandin $E_2$ (hereinafter "$PGE_2$") by murine peritoneal macrophages and suggest that M-CSF is implicated in the production of the inflammatory mediators IL-1 and $PGE_2$ and, thus, the progressive development of the inflammatory response.

DISCLOSURE OF THE INVENTION

The invention of the instant application overcomes the problems and disadvantages of the art and presents an effect that is surprising in light of the prior art by providing a method of treating a patient with inflammatory disease comprising administering an amount of macrophage-colony stimulating factor (hereinafter "M-CSF") effective to inhibit interleukin 1 (hereinafter "IL-1") biological activity. The present invention also relates to a method of treating a patient with inflammatory disease comprising administering an amount of M-CSF that is effective to cause the production of an inhibitor of IL-1. The present invention also relates to a method for inhibiting IL-1 biological activity comprising administering a pharmaceutically effective amount of M-CSF.

This invention also relates to a method of treating a patient with allergic disease comprising administering a pharmaceutically effective amount of M-CSF.

Based on excellent anti-inflammatory property and anti-allergic property of M-CSF, this invention further provides an anti-inflammatory agent and an anti-allergic agent each containing said M-CSF as an active ingredient.

Hereinafter, the above-mentioned use of treating inflammatory disease and the use of causing the production of an inhibitor of IL-1 will be described.

The accompanying drawings, which are incorporated in and constitute a part of this specification, illustrate several exemplary embodiments of the invention and, together with the description, serve to explain the principles of the invention.

DETAILED DESCRIPTION OF THE INVENTION

Figure 1:
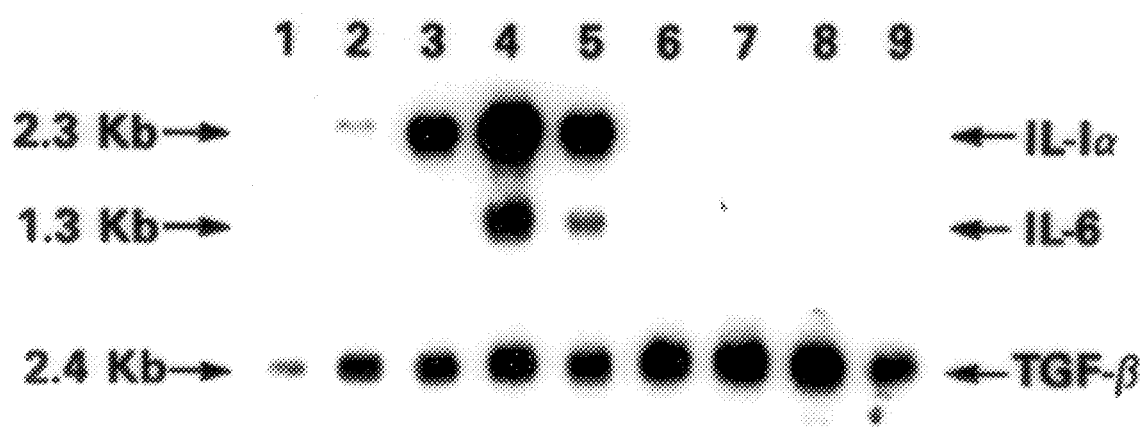
FIG. 1 depicts a Northern blot analysis of macrophage mRNA that sets forth the expression of IL-1, IL-6, and TGF-β.

Reference will now be made in detail to the presently preferred embodiments of the invention, examples of which are illustrated in the accompanying drawings.

As used in the present invention, the expression "inflammatory disease" includes but is not limited to gout, rheumatoid arthritis, ankylosine spondilitis, systemic lupus erythematosus, scleroderma, Sjogren's syndrome, mixed connective tissue disease (MCTD), Reiter syndrome, systemic necrotizing vasculitis, hypersensitivity vasculitis, temporal arteritis, Wegener's granulomatsus, sarcoidosis, Kawasaki's disease, Buerger's disease, midline granuloma, psoriatic arthritis, inflammatory diseases of the joints, insulin resistant diabetes, Hashimoto thyroiditis, juvenile autoimmune diabetes, myasthenia gravis, ulcerative colitis, cirrhosis and autoimmune uveitis.

Thus, the inflammatory conditions to be treated by the anti-inflammatory agent of the invention are not limited to the above, but include inflammatory conditions attributable to various diseases that are represented by the above-exemplified inflammatory diseases and include the allergic diseases.

As used herein, the term M-CSF refers to macrophage colony stimulating factor. In the present invention, M-CSF that can be used in the treatment of inflammatory diseases is one of a family of hematopoietic growth factors, the colony stimulating factors. Colony-stimulating factors (hereinafter "CSF") promote the growth of colonies of hematopoietic cells arising from progenitor cells of bone marrow, fetal liver and other hematopoietic organs. As indicated above, the CSF of particular interest is macrophage colony-stimulating factor (M-CSF, also known as CSF-1). M-CSF promotes the proliferation and differentiation of the mononuclear phagocyte lineage of cells, also known as macrophages. Unlike other CSF, such as granulocyte macrophage-CSF which is present only following inflammation, M-CSF is present even in noninflammatory conditions in body fluids as a result of fibroblast production.

M-CSF refers both to naturally occurring M-CSF or recombinant M-CSF, including derivatives thereof, e.g., as described in European Patent Publications No. 261592 and No. 328061; and U.S. Pat. Nos. 4,868,119 and 4,879,227. The M-CSF can be of human or any other mammalian origin, but is preferably of human origin. A particularly preferred source of natural M-CSF is the L929 fibroblast cells obtained from the American Type Culture Collection (hereinafter "ATCC").

The recombinant M-CSF and the derivatives thereof will be described below in detail. The M-CSF derivatives are designated, for convenience, with reference to the amino acid primary sequence represented by the formula (1). Formula (1):

$-32$                                                                                                          $-23$
Met—Thr—Ala—Pro—Gly—Ala—Ala—Gly—Arg—Cys—

$-13$
Pro—Pro—Thr—Thr—Trp—Leu—Gly—Ser—Leu—Leu—

$-3$
Leu—Leu—Val—Cys—Leu—Leu—Ala—Ser—Arg—Ser—

$1$                                                                                                            $8$
Ile—Thr—Glu—Glu—Val—Ser—Glu—Tyr—Cys—Ser—

$18$
His—Met—Ile—Gly—Ser—Gly—His—Leu—Gln—Ser—

$28$
Leu—Gln—Arg—Leu—Ile—Asp—Ser—Gln—Met—Glu—

$38$
Thr—Ser—Cys—Gln—Ile—Thr—Phe—Glu—Phe—Val—

-continued

Asp—Gln—Glu—Gln—Leu—Lys—Asp—Pro—Val—Cys— 48

Tyr—Leu—Lys—Lys—Ala—Phe—Leu—Leu—Val—Gln— 58

X—Ile—Met—Glu—Asp—Thr—Met—Arg—Phe—Arg— 68

Asp—Asn—Thr—Pro—Asn—Ala—Ile—Ala—Ile—Val— 78

Gln—Leu—Gln—Glu—Leu—Ser—Leu—Arg—Leu—Lys— 88

Ser—Cys—Phe—Thr—Lys—Asp—Tyr—Glu—Glu—His— 98

Asp—Lys—Ala—Cys—Val—Arg—Thr—Phe—Tyr—Glu— 108

Thr—Pro—Leu—Gln—Leu—Leu—Glu—Lys—Val—Lys— 118

Asn—Val—Phe—Asn—Glu—Thr—Lys—Asn—Leu—Leu— 128

Asp—Lys—Asp—Trp—Asn—Ile—Phe—Ser—Lys—Asn— 138

Cys—Asn—Asn—Ser—Phe—Ala—Glu—Cys—Ser—Ser— 148

Gln—Asp—Val—Val—Thr—Lys—Pro—Asp—Cys—Asn— 153    158

Cys—Leu—Tyr—Pro—Lys—Ala—Ile—Pro—Ser—Ser— 168

Asp—Pro—Ala—Ser—Val—Ser—Pro—His—Gln—Pro— 178

Leu—Ala—Pro—Ser—Met—Ala—Pro—Val—Ala—Gly— 188

Leu—Thr—Trp—Glu—Asp—Ser—Glu—Gly—Thr—Glu— 198

Gly—Ser—Ser—Leu—Leu—Pro—Gly—Glu—Gln—Pro— 208

Leu—His—Thr—Val—Asp—Pro—Gly—Ser—Ala—Lys— 214    218

Gln—Arg—Pro—Pro—Arg—Ser—Thr—Cys—Gln—Ser— 228

Phe—Glu—Pro—Pro—Glu—Thr—Pro—Val—Val—Lys— 238

Asp—Ser—Thr—Ile—Gly—Gly—Ser—Pro—Gln—Pro— 248

Arg—Pro—Ser—Val—Gly—Ala—Phe—Asn—Pro—Gly— 258

Met—Glu—Asp—Ile—Leu—Asp—Ser—Ala—Met—Gly— 268

Thr—Asn—Trp—Val—Pro—Glu—Glu—Ala—Ser—Gly— 278

Glu—Ala—Ser—Glu—Ile—Pro—Val—Pro—Gln—Gly— 288

Thr—Glu—Leu—Ser—Pro—Ser—Arg—Pro—Gly—Gly— 298

Gly—Ser—Met—Gln—Thr—Glu—Pro—Ala—Arg—Pro— 308

Ser—Asn—Phe—Leu—Ser—Ala—Ser—Ser—Pro—Leu— 318

Pro—Ala—Ser—Ala—Lys—Gly—Gln—Gln—Pro—Ala— 328

Asp—Val—Thr—Gly—Thr—Ala—Leu—Pro—Arg—Val— 338

Gly—Pro—Val—Arg—Pro—Thr—Gly—Gln—Asp—Trp— 348

Asn—His—Thr—Pro—Gln—Lys—Thr—Asp—His—Pro— 358

Ser—Ala—Leu—Leu—Arg—Asp—Pro—Pro—Glu—Pro— 368

Gly—Ser—Pro—Arg—Ile—Ser—Ser—Pro—Arg—Pro— 378

Gln—Gly—Leu—Ser—Asn—Pro—Ser—Thr—Leu—Ser— 388

Ala—Gln—Pro—Gln—Leu—Ser—Arg—Ser—His—Ser— 398

Ser—Gly—Ser—Val—Leu—Pro—Leu—Gly—Glu—Leu— 408

Glu—Gly—Arg—Arg—Ser—Thr—Arg—Asp—Arg—Arg— 418

Ser—Pro—Ala—Glu—Pro—Glu—Gly—Gly—Pro—Ala— 428

Ser—Glu—Gly—Ala—Ala—Arg—Pro—Leu—Pro—Arg— 438

Phe—Asn—Ser—Val—Pro—Leu—Thr—Asp—Thr—Gly— 448

His—Glu—Arg—Gln—Ser—Glu—Gly—Ser—Ser—Ser— 458

Pro—Gln—Leu—Gln—Glu—Ser—Val—Phe—His—Leu— 468

Leu—Val—Pro—Ser—Val—Ile—Leu—Val—Leu—Leu— 478

Ala—Val—Gly—Gly—Leu—Leu—Phe—Tyr—Arg—Trp— 488

Arg—Arg—Arg—Ser—His—Gln—Glu—Pro—Gln—Arg— 498

Ala—Asp—Ser—Pro—Leu—Glu—Gln—Pro—Glu—Gly— 508

Ser—Pro—Leu—Thr—Gln—Asp—Asp—Arg—Gln—Val— 518

Glu—Leu—Pro—Val 522 wherein X represents Tyr or Asp.

Thus, on the basis of the amino acid sequence from Glu at position 1 to Val at position 522 of the formula (1), there are shown various derivatives obtained by modifying said amino acid sequence, for example, by replacements, deletions and additions. When desired, these derivatives are abbreviated in accordance with a conventional manner. For example, M-CSF-(3-153) or M-CSF-(4-153) represents an active derivative consisting of a polypeptide having an amino acid sequence from Val at position 3 or from Ser at position 4 to Thr at position 153 of the formula (1).

The recombinant M-CSF and the derivatives thereof are suitably used in the invention so far as they possess the physiological activities of M-CSF per se. Preferred are M-CSF having the total amino acid primary sequence of the formula (1), or M-CSF having an amino acid primary sequence wherein the N-terminus exists in the region from Glu at position 1 to Glu at position 5 of the formula (1) and the C-terminus exists in the region from Thr at position 153 to Val at position 522 and wherein the N-terminus may have Met as added thereto. Particularly preferred examples include, for example, biologically active M-CSF derivatives and recombinant M-CSF having an amino acid primary sequence extending from Val at position 3 or Ser at position 4 to Thr at position 153 or Pro at position 214 of the formula (1), which may have Met added to the N-terminus.

In contrast to the art discussed above, as set forth in in vitro assays to measure expression of IL-1 and IL-6 in macrophages treated with LPS, the M-CSF of the present invention does not promote the gene expression of either IL-1 or IL-6. In addition, as measured by in vitro assays, the M-CSF of the present invention does not promote the production of IL-1, IL-6, or $PGE_2$ from macrophages treated with LPS.

Instead, the M-CSF of the present invention can be used in the treatment of patients diagnosed with inflammatory disease by administration in an amount that is effective to inhibit IL-1 bioactivity. For example, as set forth in the following examples, both pretreatment and cotreatment with M-CSF can inhibit the production of bioactive IL-1 produced in response to lipopolysaccharide (hereinafter "LPS"), a bacterial endotoxin known as a potent stimulator of macrophage function in vitro. Similarly, as set forth in the following examples, pretreatment with M-CSF can inhibit the production of bioactive IL-1 produced in response to LPS in vivo.

The M-CSF of the present invention can also be used to treat a patient diagnosed with inflammatory disease by administering an amount of M-CSF that is effective to cause the production of an inhibitor of IL-1. As set forth in the following examples, administration of M-CSF appears to stimulate the production of an inhibitor of IL-1 that reduces the bioactivity of IL-1 in response to treatment with LPS in vitro. As used herein, interleukin-1 (hereinafter "IL-1") is a factor which is produced by macrophages, particularly after interacting with immune complexes, bacterial products or T cells. IL-1 promotes thymocyte proliferation and mature T cells to release their own growth-promoting molecules. IL-1 also induces fever. Fever is considered an acute response to antigen that results in higher T cell activity.

As discussed above, IL-1 is a protein mediator of inflammation. As set forth in Larrick, J. W. et al., "The role of tumor necrosis factor and interleukin-1 in the inflammation response," a review in *Pharmaceutical Research* 5(3): 129–139 (1988), IL-1 modulates the inflammatory function of endothelial cells, leukocytes, and fibroblasts and may promote the accumulation of granulocytes at sites of inflammation. See also C. P. J. Maury, "Interleukin 1 and Pathogenesis of Inflammatory Diseases," *Acta Med Scand* 220: 291–4 (1986).

IL-1 means natural occurring IL-1α, naturally occurring IL-1β, recombinant IL-1α, recombinant IL-1β, and derivatives of IL-1α or IL-1β such as described in European Patent Publication 237073, European Patent Publication 237967, PCT Publication 89/01946 (also see Oppenheim, J. J. et al., *Immunol. Today* 7: 45 (1986)). The IL-1 can be of human or any other mammalian origin, preferably human origin.

As used herein, the term "IL-1 inhibitor" refers to an agent that is able to inhibit the biological activity of IL-1, such as in the mediation or progression of inflammation. Inhibition of biological activity can be assessed using any number of assays for IL-1 activity with which those of ordinary skill in the art would be familiar, such as the IL-1 bioassay described by Togawa, A. et al., "Characterization of Lymphocyte Activating Factor Produced by Human Mononuclear Cells; Biochemical Relationship of High and Low Molecular weight Forms of LAF," *J. Immunol.* 122: 2112 (1979).

Additionally, the IL-1 inhibitor of the invention refers to an agent that is able to bind to the IL-1 receptor. Such a characteristic can be easily determined by those of ordinary skill in the art, using techniques, for example, as described by Kilian, T. L., et al., "Interleukin 1 Alpha and Interleukin 1 Beta Bind to the Same Receptor on T Cells," *J. Immunol.* 136: 4509 (1986).

The production of the IL-1 inhibitor of the present invention is affected by M-CSF. In a preferred embodiment, the IL-1 inhibitor is regulated by M-CSF so that administration of increasing doses of M-CSF causes a greater inhibition in IL-1 bioactivity.

In an additional preferred embodiment, the inhibitor is specific to IL-1 and will not regulate the activity of IL-2, IL-6 or TNF (tumor necrosis factor).

The present invention relates to the inhibition of IL-1 biological activity by administering a pharmaceutically effective amount of M-CSF. As used herein, pharmaceutically effective refers to an amount of an agent that is able to reduce any of the symptoms of the inflammatory diseases described above. As is known by those of ordinary skill in this art, symptoms of inflammatory disease include erythema, edema, tenderness (hyperalgesia), and pain. The dosage of M-CSF that may reduce these symptoms range from 1 μg/kg to 100 mg/kg, with a particularly preferred dosage of 1 mg/kg to 35 mg/kg.

Persons of ordinary skill in the art would be able to optimize the dosage of the M-CSF or IL-1 inhibitor of the instant invention using techniques that are known in the art. Those techniques are set out, for example, on pages 19–28 of Goodman and Gilman, *The Pharmacological Basis of Therapeutics*, 5th Ed. (1975). Dosages can be ascertained and optimized through the use of the established assays and conventional dose-response studies. Further refinements of the calculations necessary to determine the appropriate dosage for treatment are routinely made by those of ordinary skill in the art and are within the array of tasks routinely performed by them without undue experimentation. In addition, the dosage of M-CSF or IL-1 inhibitor to be administered in the methods of the present invention will vary depending upon, for example, the particular inflammatory disease to be treated, the mode of administration, the age, the weight and the sex of the subject to be administered.

The present invention envisions any mode of administering either M-CSF or the IL-1 inhibitor. Examples of such modes of-administration include intravenous, intramuscular, local, transdermal, injection, oral and parenteral. A preferred administration is a local administration to the site.

The M-CSF and IL-1 inhibitor of the present invention can be administered alone or in combination with any of the conventional anti-inflammatory agents discussed above.

Appropriate pharmaceutically acceptable carriers, diluents and adjuvants can be used together with the compounds described herein to prepare the desired compositions for use in the treatment of patients. The pharmaceutical compositions of this invention will contain the M-CSF or the IL-1 inhibitor compound together with a solid or liquid pharmaceutically acceptable nontoxic carrier. Such pharmaceutical carriers can be sterile liquids, such as water and oils, including those of petroleum, animal, vegetable or synthetic origin, such as peanut oil, soybean oil, mineral oil, sesame oil and the like. Water is a preferred carrier when the pharmaceutical composition is administered intravenously. Saline solutions and aqueous dextrose and glycerol solutions can also be employed as liquid carriers, particularly for injectable solutions. In addition, the compounds of the instant application can be associated with liposomes, as set forth in copending U.S. application Ser. No. 07/505,584, to Gideon Strassmann, filed Apr. 6, 1990, now abandoned hereby specifically incorporated by reference. Suitable pharmaceutical excipients include starch, glucose, lactose, sucrose, gelatin, malt, rice, flour, chalk, silica gel, magnesium carbonate, magnesium stearate, sodium stearate, glycerol monostearate, talc, sodium chloride, dried skim milk, glycerol, propylene glycol, water, ethanol and the like. These compositions can take the form of solutions, suspensions, tablets, pills, capsules, powders, sustained-release formulations and the like. Suitable pharmaceutical carriers are described in "Remington's Pharmaceutical Sciences" by E. W. Martin. Such compositions will contain an effective therapeutic amount of the active compound together with a suitable-amount of carrier so as to provide the form for proper administration to the patient. The compounds of the present invention can be used in the treatment of patients. Patients shall be used in its broadest sense to mean mammals, including humans, as well as animals, for example, dogs, cats, guinea pigs, mice, and rats.

As already stated, this invention also relates to a use of an anti-allergic composition comprising, as an active ingredient, the M-CSF specified in this specification including M-CSF derivatives such as biologically active recombinant human M-CSF derivatives having an amino acid sequence extending from Val at 3-position or Ser at 4-position to Thr at 153-position or Pro at 214-position of the formula (1), which may have Met added to the N-terminus.

Hereinafter, the process for preparing a M-CSF-derivative used as an active ingredient in the invention are described in detail. Said derivative is prepared utilizing a gene coding for the same, i.e. by preparing a recombinant DNA for the expression of said gene in host cells, introducing the DNA into host cells for transformation thereof and cultivating the resulting transformant.

The gene for the production of a human M-CSF derivative of the present-invention can be prepared starting with mRNA isolated from various human cells having ability to produce M-CSF, more specifically and advantageously from the AGR-ON [human leukemic T cell-derived cultured cell line having the characteristics described in Unexamined Japanese Patent Publication SHO 59-169489; deposited in the American Type Culture Collection (ATCC) under the ATCC deposition No.CRL-8199]. The extraction procedure for the isolation of mRNA from said AGR-ON can be carried out, for example by the guanidinium/hot phenol method [T. Maniatis, E. F. Fritsch and J. Sambrook, Molecular Cloning, pp. 194–195 (Cold Spring Harbor Laboratory), 1982], the guanidinium/cesium chloride method [T. Maniatis, E. F. Fritsch and J. Sambrook, Molecular Cloning, p. 196 (Cold Spring Harbor Laboratory), 1982] or the like. The conversion of the purified mRNA to cDNA, namely the synthesis of the desired gene, can be realized, for example by the Okayama-Berg method [H. Okayama and P. Berg, Molecular and Cellular Biology, vol. 3, p. 280 (1983)], the Gubler-Hoffman method [V. Gubler and B. J. Hoffman, Gene, vol. 25, pp. 263–269 (1983)] or the like. The transformation by introducing the thus-obtained DNA into host cells and the selection of a desired strain carrying the M-CSF cDNA from among the transformants can be performed by conventional methods. Unexamined Japanese Patent Publication HEI 1-104176 describes these procedures or methods in detail. The M-CSF gene described in said patent specification also can be advantageously employed as the M-CSF gene to be used in the practice of the present invention.

The genes mentioned above can also be prepared in the manner of chemical synthesis of nucleotides using a conventional method such as the phosphite triester method [Nature, 31, 105 (1984)]. In any of the methods, various procedures or steps, such as partial DNA synthesis by chemical means, enzyme treatments for DNA chain cleavage, deletion, addition and ligation, DNA isolation, purification and replication, screening, etc., can be performed in the conventional manner. For example, the above-mentioned DNA isolation and purification can be carried out by agarose gel electrophoresis, etc., and partial modification of a codon in the nucleic acid sequence can be conducted by site-specific mutagenesis [Proc. Natl. Acad. Sci., 81, 5662–5666 (1984)), etc. The codon to be selected for a desired amino acid is not limited specifically but can be determined in a usual manner in view of the codon usage for the host cell to be utilized, etc. The DNA sequence of the desired gene to be used in the above methods can be determined and confirmed, for example, by the Maxam-Gilbert chemical modification method [Methods in Enzymolozy, 65, 499–560 (1980)] or by the dideoxynucleotide chain termination method using M13 phage [Messing, J. and Vieira, J., Gene, 19, 269–276 (1982)].

The M-CSF derivatives of the present invention can be produced easily in large Quantities by recombinant DNA techniques using the genes obtained in the above manner. While the use of the above-mentioned specific genes is essential, this process can be conducted basically by general genetic engineering techniques [cf. Molecular Cloning, T. Maniatis et al., Cold Spring Harbor Laboratory (1982), etc.].

More specifically, a recombinant DNA which enables the expression of an M-CSF gene in host cells is produced, and the DNA is introduced into the host cell for transformation thereof and the transformant is cultivated.

Useful host cells can be either eukaryotic or prokaryotic cells. Generally used as the prokaryotic hosts are *E. coli* and *Bacillus subtilis*. In the practice of the invention, a plasmid vector capable of replication in such a host, for instance, is employed and, for enabling expression of an M-CSF gene in said plasmid vector, an expression vector can be used which contains a promoter and an SD (Shine-Dalgarno) sequence and further an initiation codon (e.g. ATG) required for the initiation of protein synthesis upstream from said gene. Widely used as host *E. coli* is the strain K12. pBR322 is generally used as the vector. However, these are not limitative but various known strains and vectors can be used. Useful as the promoter are, for example, the tryptophan (trp) promoter, lpp promoter, lac promoter, $P_L$ promoter, etc. and, in any case, the desired gene can be expressed.

As a preferred process for producing the human M-CSF derivatives of the present invention using the genes mentioned above, there may be mentioned, by way or example, a process which uses a prokaryotic host, such as *E. coli*, as the host and in which the desired protein is expressed by the two-cistron technique. This is a gene expression system comprising two cistrons in sequence and the process yields and accumulates the desired human M-CSF derivative stably in large quantities in host cells.

The production of an M-CSF derivative of the present invention by said two-cistron method is now described in detail. First, an expression plasmid is prepared which contains two cistrons, namely a gene as the first cistron coding for an appropriate polypeptide and an M-CSF gene as the second cistron. It is important that the plasmid should contain, upstream from the first cistron, a promoter and an SD sequence for the expression of said gene and further contain, downstream from the first cistron but upstream from the second cistron, a synthetic linker which contains an SD sequence for the expression of the second cistron, a termination codon for the first cistron and an initiation codon for the second cistron, as arranged in this order.

The gene to be used as the first cistron may be a synthetic or natural gene insofar as the gene can be expressed in the host. Since the expression of said gene leads to production of a polypeptide different from the M-CSF derivative in the same system and this makes it necessary to separate said polypeptide, it is desirable that said polypeptide should be hydrophobic and have a molecular weight greatly different from that of the M-CSF derivative. It is desired that the above-mentioned first cistron should code for such a polypeptide. As preferred examples of the first cistron, there may be mentioned genes coding for IL-2, IFN-$\alpha$, -$\beta$ and -$\gamma$, etc. and fragments derived from these genes and coding for about 50 to 100 amino acid residues.

The promoter and SD sequence to be arranged upstream from the first cistron may be per se known ones. Examples of such promoter are the trp promoter, tac promoter, $P_L$ promoter, $P_R$ promoter, lpp promoter, OmpA promoter, lac promoter, etc., among which the trp promoter, $P_L$ promoter, $P_R$ promoter and the like are particularly preferred. Examples of the SD sequence are sequences of 3 to 9 base pairs, such as GGAG and AGGA, that are capable of forming a hydrogen bond with the 3' terminus of 16S rRNA of prokaryotic cells.

The initiation codon and the termination codon to be present in the synthetic linker between the first cistron and the second cistron can be any of the naturally occurring ones. These codons need not be used each in a complete form, for example as TGA and ATG, but can be used in a partly overlapping form, for example as TGATG, TAATG, etc. The expression plasmid for use in the above two-cistron method can be constructed by a usual method.

A method, which can be mentioned as a particularly preferred example, comprises first cleaving an M-CSF gene-containing plasmid with a suitable restriction enzyme, isolating and purifying the resulting M-CSF gene-containing fragment by a usual method, separately synthesizing the above-mentioned synthetic linker by a usual method, for example by using a DNA synthesizer, joining the linker to the fragment obtained in the above manner on the upstream side of the M-CSF gene using T4 DNA ligase or the like, and incorporating the resulting DNA fragment into a plasmid containing the first cistron and capable of expressing the same, at a proper position. Alternatively, an expression plasmid suitable for-the-desired two-cistron system can be prepared from the DNA fragment obtained by the above method and containing the second cistron as joined to the synthetic linker, by joining the first cistron to the upstream end of said fragment, and introducing the resulting DNA fragment into a plasmid having a suitable protein expression system.

The plasmid thus obtained is introduced into suitable host cells for transformation of the cells, whereby the desired transformant can be obtained through the two-cistron method. When such transformant is used, the protein relating to the first cistron and the desired M-CSF derivative relating to the second cistron can be expressed individually. These products can be analysed or identified by a usual method, for example by SDS-PAGE, Western blotting or the like, and can be separated from each other and purified by the various methods described later herein.

The desired transformant thus obtained can be cultivated by a usual method, whereby the human M-CSF derivative is produced and accumulated. The medium to be used for said cultivation may be one suitably selected from among those usually used for the host cell employed. For cultivating the transformant using E. coli or the like as the host, for example, LB medium, E medium, M9 medium, M63 medium and the like can be used. Various carbon sources, nitrogen sources, inorganic salts, vitamins, cell extracts, physiologically active substances, etc., which are generally known, can be added to these media when required.

In cultivating the above transformant, those cultivation conditions that are suited for the growth of host cells can be employed. In the case of E. coli, for instance, a pH of about 5–8, preferably 7 or about 7, and a temperature of about 20°–43° C., preferably 37° C. or about 37° C., can be employed.

In the above manner, the desired M-CSF derivative of the present invention is produced and accumulated in the transformant cells. This derivative can be isolated and purified by various separation procedures utilizing the physical, chemical or other properties thereof. As typical examples of said procedures, there may be mentioned usual refolding treatment, treatment with a protein precipitating agent, centrifugation, osmotic shock method, ultrasonication, ultrafiltration, molecular sieve chromatography (gel filtration), adsorption chromatography, ion-exchange chromatography, affinity chromtography, high-performance liquid chromatography (HPLC), various other liquid chromatographic techniques, dialysis, and combinations of these. By using such separation procedures, the desired human M-CSF derivative can be produced easily in high yields with high purity on a commercial scale.

The thus-obtained M-CSF derivatives of the present invention are in common in that they have CSF activity although they differ slightly in N-terminal amino acid sequence, molecular Freight, etc. depending on the gene used for the production and on the expression system for the expression of said gene and, especially, may have a Met residue corresponding to the initiation codon as added to the N-terminus in the process of expression of the derivatives of the invention.

Preferred as the active ingredient of the anti-allergic composition according to the invention are M-CSF derivatives wherein the N-terminus exists in any position of the region from Glu at 1-position to Glu at 5-position of the formula (1) (said N-terminus may have Met as added thereto), and wherein the C-terminus exists in any position of the region from Thr at 153-position to Val at 522-position of the formula (1).

Of these derivatives, particularly preferred are, as stated above, M-CSF derivatives having an amino acid primary sequence extending from Val at 3-position or Ser at 4-position to Thr at 153-position or Pro at 214-position of the formula (1), wherein the N-terminus may have Met as added thereto.

Also usable is a M-CSF derivative having a total amino acid sequence extending from Met at position −32 to Val at position 522 of the formula (1).

The anti-allergic agent of the invention is usually formulated into a pharmaceutical composition containing an effective amount of M-CSF including the M-CSF derivatives obtained above in combination with a conventional pharmacologically acceptable non-toxic carrier, and is administered by various routes depending on the form of the composition.

Such compositions are for example, in the form of liquid preparations including solutions, suspensions, emulsions and the like, which are usually given orally, intravenously, subcutaneously, intracutaneously or intramuscularly. Such forms or methods of administration are not limited specifically. The derivatives can also be prepared in other various preparation forms usually used and suited, for example, to oral or parenteral administration. The compositions can be provided also as dry preparations which can be reconstituted to liquids by addition of a suitable carrier. While the dose of each preparation is not limited specifically but can be determined suitably depending on the desired pharmacological effect, the kind of disease, the age and sex of the patient, the severity of disease, etc., the preparation is administered generally at such a dose that the active ingredient is administered in an amount of about 0.001 to about 1 mg/kg/day calculated as the amount of protein. The composition may be given daily either in a single dose or in several divided doses.

When a biologically active M-CSF derivative having an amino acid primary sequence extending from Val at 3-position or Ser at 4-position to Thr at 153-position of the formula (1) which may have Met as added to the N-terminus is used as the active ingredient M-CSF in the invention, the resulting composition not only possesses its own anti-inflammatory and anti-allergic properties, but also has a feature of exhibiting a higher bioavailability compared with other M-CSF. Thus such anti-inflammatory and anti-allergic compositions are very useful from this view point as well.

The invention will be further clarified by the following examples, which are intended to be purely exemplary of the invention.

In the following EXAMPLES and REFERENCE EXAMPLES, each of the M-CSF derivatives designated with reference to the amino acid sequence of the formula (1) is one wherein X in said formula represents Asp.

EXAMPLE 1

Figure 2:
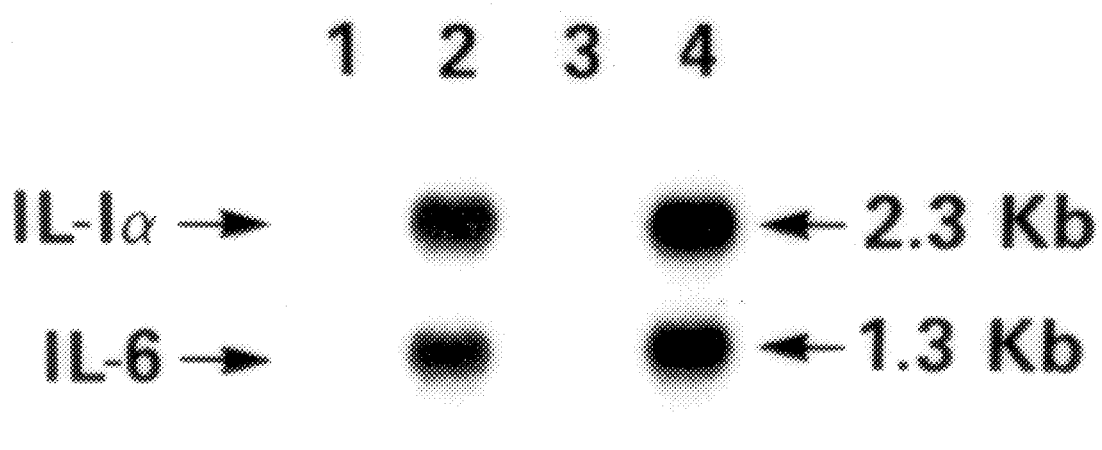
FIG. 2 is a radioautograph that depicts the expression of IL-1α and IL-6 mRNA obtained from macrophages treated with LPS and M-CSF and a combination of LPS and M-CSF.

M-CSF does not stimulate the production of the inflammatory mediators IL-1, IL-6, and $PGE_2$ As set forth in FIGS. 1 and 2 and Table 1, M-CSF does not promote the production in macrophages of the inflammatory mediators IL-1α, $PGE_2$, and IL-6.

A. M-CSF does not promote expression of IL-1 or IL-6

1. The experimental model

Lipopolysaccharide (hereinafter "LPS"), the active component of endotoxin derived from bacterial cells, was employed as the model system to demonstrate the effects of M-CSF on the production of inflammation mediators in inflammatory macrophages.

To obtain inflammatory macrophages, macrophages were harvested from inbred female pathogen-free C57B1/6 mice (Charles River Breeding Laboratories, Wilmington, Mass.) 3 days after the mice were injected with 1.0 ml of sterile Brewer's thioglycollate (TG). The cells were obtained by peritoneal lavage with 10 ml of ice cold HBSS (Hanks' Balanced Salt Solution) supplemented with 10 U/ml of heparin and centrifuged at 250×g for 5 min. at 4° C.

The resulting cell pellet was resuspended in RPMI 1640 medium (GIBCO, Grand Island, N.Y.) supplemented with 10% (v/v) of heat-inactivated, low endotoxin (0.008 ng/ml), fetal calf serum (Hyclone, Logan, Vt.), 2.0 mM glutamine, 100 U/ml of penicillin and 100 μg/ml of streptomycin (hereinafter "complete medium").

1.0 ml aliquots of $0.5 \times 10^6$ macrophages were plated per 16 mm well ($2.5 \times 10^5$ macrophages/cm$^2$) in tissue culture dishes (Costar, Cambridge, Mass.). The dishes were incubated for 2.0 hours at 37° C. in 6.0% $CO_2$, and washed 3 times with warm (37° C.) complete medium to remove non-adherent cells. The cell monolayers contained approximately 95% macrophages, as determined by non-specific esterase staining.

The cells were exposed at 37° C. to LPS and M-CSF as set forth below in sections 2 and 3. The resulting conditioned medium was collected by centrifugation at 570×g for 15 min at 4° C., dialyzed against 100 volumes of RPMI 1640 medium, filter sterilized and stored at −35° C. for further analysis.

2. M-CSF does not promote expression of IL-1 or IL-6

The inflammatory macrophages were exposed to a control; to LPS (0.5 μg/ml obtained from E. coli 0.55:B5 (Difco, Detroit, Mich.)); and to M-CSF (0.5 μg/ml of recombinant M-CSF-(3-153) with specific activity of $2.7 \times 10^7$ U/mg (Batch 058-2) produced as described in Takahashi, M. et al., Biochemical and Biophysical Research Communications 161 (2): 892–901 (Jun. 15, 1989) and purified as in Reference Example 4 to be described below for varying times as follows. 1.0 unit of M-CSF is defined as the half maximal stimulation-of growth of the M-CSF dependent human cell line NFS-60, Nakoinz, I. et al., Exp. Hemotol. 17: 669 (1989).

| Tube | Contents | Time (hours) |
|---|---|---|
| 1 | Control | 6.0 |
| 2 | LPS (5 μg/ml) | 0.75 |
| 3 | LPS (5 μg/ml) | 1.5 |
| 4 | LPS (5 μg/ml) | 3.0 |
| 5 | LPS (5 μg/ml) | 6.0 |
| 6 | M-CSF (058-2 0.5 μg/ml) | 0.75 |
| 7 | M-CSF (058-2 0.5 μg/ml) | 1.5 |
| 8 | M-CSF (058-2 0.5 μg/ml) | 3.0 |
| 9 | M-CSF (058-2 0.5 μg/ml) | 6.0 |

IL-6 and TGF-β using the Northern Analysis of macrophage mRNA. Such an analysis is among the routine skills of those in this art and is described, for example in Section XI., Nucleic Acid Hybridization: Determination of Genetic Homology in Recombinant DNA Methodology, Dillon J. R., A. Nasim, E. R. Nestmann (eds) John Wiley & Sons (1985).

The sections designated IL-1α and IL-6 of FIG. 1 indicate that LPS can promote the expression of both IL-1α and IL-6. Compare the control (lane 1) with samples that received LPS alone (lanes 2–5). The expression of both IL-1α and IL-6 increased with time but peaked at 3 hours.

In contrast, the presence of M-CSF (lanes 7–10) did not promote the expression of either IL-1α or IL-6. Both those lanes are blank.

As can be seen in the section designated TGF-β, TGF-β was expressed by LPS, as well as M-CSF, indicating that all the proteins were active.

This experiment was repeated twice with identical results. Thus, unlike LPS which does promote the production of inflammatory mediators, M-CSF does not stimulate the production of IL-1 or IL-6. This finding is surprising in light of earlier reports that indicated that M-CSF stimulated the production of IL-1.

3. M-CSF does not stimulate IL-1α gene expression

An experiment conducted with a different preparation of M-CSF confirmed the inability of M-CSF to induce gene expression of IL-1. In FIG. 2, a different preparation of M-CSF was tested and found not to stimulate IL-1α expression.

Inflammatory macrophages were exposed to a control (lane 1), to LPS at 1 μg/ml (obtained as above) (lane 2), to M-CSF-(3-153) at 1 μg/ml (obtained as above except a different batch with a specific activity of $3.0 \times 10^7$ U/mg) (lane 3), and to a combination of LPS and M-CSF (lane 4). The cells were analyzed for expression of IL-1α as set forth in Molecular cloning: a laboratory manual, T. Maniatis, E. F. Fritsch, J. Sambrook (eds) Cold Spring Harbor Press (1982).

Compared to the control lane (1), LPS (in lane 2) did stimulate the expression of IL-1α gene, M-CSF (in lane 3) did not stimulate the expression of IL-1α, and the addition of M-CSF to LPS (in lane 4) did not affect the expression of IL-1α. Thus, as set forth in section 1 above, M-CSF neither induces nor reduces the expression of IL-1α.

B. M-CSF does not promote the activity of IL-1, IL-6, or $PGE_2$

1. The experimental model a. Conditioned media

Inflammatory macrophages, obtained as set forth above, were treated with M-CSF from two sources to yield conditioned media as follows:

recombinant M-CSF-(3-153) (Batch EC-80-I) with specific activity of $3.0 \times 10^7$ U/mg and produced as above; and natural M-CSF with a specific activity of $1.5 \times 10^{10}$ U/mg derived from L929 fibroblasts (obtained from E. R. Stanley (Albert Einstein College of Medicine, NY)).

The cells were exposed to increasing doses of both sources of M-CSF up to a maximum dose of 1 µg/ml. After an incubation period of 24 hours, the conditioned medium was analyzed for the activity of IL-1, IL-6, and $PGE_2$ as set forth below.

b. The IL-1 thymocyte assay

To assess the effect of the conditioned media on the production of bioactive IL-1, the cells were subjected to a thymocyte assay as described by Togawa, A., et al., "Characterization of Lymphocyte Activating Factor Produced by Human Mononuclear Cells; Biochemical Relationship of High and Low Molecular Weight Forms of LAF," *J. Immunol.* 122: 2112 (1979). In this assay, a single cell suspension of thymocytes, obtained from female C3H/He mice (Bantin-Kingman (CA)) 6 to 10 weeks of age, was prepared by gentle mincing. Large aggregates were removed by incubation on ice for 10 min. at unit gravity. The cells were washed twice with complete medium and resuspended to a density of $1.0 \times 10^2$ cells/ml in complete medium. The cells were thereafter seeded in flat-bottomed microtiter plates at a density of $1.0 \times 10^6$ cells/well in the absence or presence of 1 µg/ml of Concanavalin A (hereinafter "ConA") (Sigma Chemical Co.).

Either conditioned medium or recombinant human IL-1β was added in serial dilutions to a final volume of 0.2 ml. The thymocytes were cultured for 72 hours and pulsed with 1.0 µCi of [methyl]-$^3$H-TdR (6.7 Ci/Mmol, New England Nuclear, Boston, Mass.). $^3$H-TdR incorporation was determined by standard liquid scintillation counting procedures after harvest of the cells on glass fiber paper using a semiautomatic cell harvester (Skatron, Sterling, Va.).

As set forth in Table 1 below, neither the natural M-CSF (designated M-CSF Type L929) nor the recombinant M-CSF-(3-153) (designated *E. coli*[3-153]M-CSF or rh-M-CSF (3-153)) exhibited positive results in the assay, indicating the neither source of M-CSF could produce IL-1 in inflammatory macrophages.

c. The IL-1 radioreceptor assay

The observation that both human IL-1α and IL-16 bind to the same receptor as murine IL-1 on murine EL-4.6.1 target cells led to the development of the IL-1 receptor assay described by Kilian, T. L., et al., "Interleukin 1 Alpha and Interleukin 1 Beta Bind to the Same Receptor on T Cells," *J. Immunol.* 136: 4509 (1986). In the assay, murine EL-4.6.1 cells from the ATCC, maintained in complete medium, were centrifuged and resuspended in binding buffer comprising RPMI 1640 medium supplemented with 0.1 mg/ml of bovine serum albumin and 25 nM HEPES (pH 7.2). Cell density was adjusted to $8.0 \times 10^6$ cells/ml and 0.05 ml aliquots were dispensed into tubes placed on ice.

275 pg of $^{125}$I-IL-1α (75000 cpm) (specific activity, 2000 Ci/mmol; Amersham, Arlington Heights, Ill.) was added to each tube. The tubes were then incubated for 3.0 hours at 4° C. with diluted conditioned medium from macrophages treated with up to 1.0 µg/ml of the two sources of M-CSF.

Non-specific binding was determined by the addition of 5.8 pM recombinant human IL-1β (specific activity, $4.0 \times 10^7$ U/mg; obtained from Hirai (Otsuka Pharmaceutical, Tokushima, Japan)). To separate $^{125}$I-IL-1α which was bound to the cells from free $^{125}$I-IL-1α, 0.2 ml of an oil mixture of dibutyl phthalate and dioctyl phthalate (10:1 (v.v)) was injected into each assay tube and each tube was centrifuged for 2.0 min at 4° C. in a macrofuge. The fluid was then aspirated, the tube tips were cut and cell bound radioactivity was determined in a gamma counter.

As set forth in Table 1 below, neither type of M-CSF could displace the IL-1, indicating that neither type of M-CSF stimulated the production of IL-1 in the macrophages.

d. IL-1 mRNA assay

The expression of IL-1 mRNA was determined as above. As in FIG. 1, Table 1 indicates that neither the recombinant M-CSF nor the natural M-CSF was able to promote the expression of IL-1 from the macrophages, confirming that neither type stimulated the production of IL-1 in the macrophages.

e. IL-6 B-9 assay

The IL-6 assay employed was that described by Aarden et al., *Eur. J. Immunol.*, 17: 1411–1416 (1987) as follows. The IL-6 dependent hybridoma cell line B13.29 clone B9 was maintained in Iscove's modified Dulbecco's medium supplemented with 2.0% (v/v) MG63 osteocosarcoma from ATCC conditioned medium as a source of IL-6. To these cells was added 5.0% (v/v) fetal calf serum, 50 µM β-mercaptoethanol, 100 U/ml of penicillin and 100 mg/ml of streptomycin. $5.0 \times 10^4$/ml of clone B9 cells were cultured in 0.2 ml of above medium in flat-bottomed 96 well plates (Falcon). Conditioned media was added to the cells and the plates were incubated for 72 hours in an atmosphere of 5.0% $CO_2$, in air at 37° C. The plates were incubated with 1.0 µCi [$^3$H]-thymidine for the last 4 hours of the culture period. The cells were then harvested using a cell harvester (Skatron, Sterling, Va.) and the [$^3$H]-thymidine which had been incorporated into DNA was quantitated by a liquid scintillation counter (LKB RockBeta). The samples were tested in duplicate, titrated in 3-fold dilutions. All of the assays were compared to a standard curve using $1.0 \times 10^7$ U/mg of recombinant human IL-6 (Amgen, Thousand Oaks, Calif.).

As set forth in Table 1, neither the recombinant M-CSF nor the natural M-CSF was able to stimulate the production of IL-6, indicating the neither form could stimulate the production of IL-1 in macrophages.

f. IL-6 mRNA assay

The expression of IL-6 mRNA was determined as above and confirmed the results obtained with the B-9 assay. As set forth in Table 1, neither form of M-CSF was able to stimulate the expression of IL-6.

g. $PGE_2$ assay

In order to determine the ability of M-CSF to stimulate the production of $PGE_2$, the presence of $PGE_2$ was determined as follows. The conditioned medium from macrophages treated with up to 1.0 µg/ml of both recombinant and natural M-CSF was diluted with phosphate buffered saline (PBS), acidified to approximately pH 2 and extracted with an equal amount of chloroform:methanol (1:1 (v/v)). The organic phase was dried under nitrogen and quantification of $PGE_2$ was determined by a standardized radioimmunoassay kit purchased from New England Nuclear, Boston, Mass.

As set forth in Table 1 below, as with IL-1 and IL-6, neither form of M-CSF could stimulate the production of $PGE_2$.

TABLE 1

Production of Inflammatory Mediators by Macrophage in Response to M-CSF

| Inflammatory Mediators | Assay | M-CSF Type L929 | rh M-CSF (3-153) |
|---|---|---|---|
| IL-1α | Thymocyte | No | No |
| | Radioreceptor | No | No |
| | mRNA | No | No |
| PGE$_2$ | RLA | No | No |
| IL-6 | B-9 | No | No |
| | mRNA | No | No |

As indicated by the above experiments, M-CSF does not stimulate the production of inflammatory mediators such as IL-1, IL-6, or PGE$_2$.

EXAMPLE 2

M-CSF regulates the production of inflammatory mediators produced in response to LPS treatment As set forth in FIGS. 2–10 and Tables 2–3 and as set forth below in detail, M-CSF is able to decrease the activity of the inflammatory mediators IL-1 and PGE$_2$ produced in response to LPS.

A. M-CSF regulates the production of PGE$_2$

1. Pretreatment with M-CSF reduces PGE$_2$ production

Macrophages were obtained as in Example 1 and divided into four sets. Two sets of macrophages were pretreated with culture medium and two were pretreated with recombinant M-CSF obtained as in Example 1. In the treatment phase, one set of cells pretreated with medium and one set of cells pretreated with M-CSF received LPS at 1 μg/ml as set forth in Table 2 below. The other set received medium. The presence of PGE$_2$ was determined as described in Example 1, and expressed in ng/mg(cell protein)/24 hr. or ng/ml/24 hr.

As set forth in Table 2a, the control levels of PGE$_2$ when pretreated with either medium or M-CSF is 0.11–0.12. LPS treatment of cells pretreated with medium yields PGE$_2$ levels of approximately 10.00, a nearly 100 fold increase over control levels. When LPS is added to cells pretreated with M-CSF, however, the increase in PGE$_2$ levels is inhibited by 65% to only a level of approximately 3.6.

Thus, it appears that pretreatment with M-CSF Will block the capacity of LPS to stimulate PGE$_2$ levels.

TABLE 2a

Pretreatment or Co-Treatment of M-CSF Reduces LPS induced PGE$_2$ Formation by Macrophages

| Pretreatment | Treatment | PGE$_2$ (ng/mg/24 h.) ± S.D. | % Inhibition |
|---|---|---|---|
| Medium | Medium | 0.11 | — |
| Medium | LPS (1 μg/ml) | 10.0 | — |
| M-CSF (rh)** | Medium | 0.12 | — |
| M-CSF (rh)** | LPS (1 μg/ml) | 3.6 | 65 |

**E. coli[3-153]M-CSF (M-CSF-(3-153))

2. Pretreatment or cotreatment with M-CSF reduces PGE$_2$ production

Macrophages obtained as in Example 1 were pretreated either with culture medium or M-CSF as set forth in Table 2 below. Both recombinant M-CSF-(3-153) (designated "rh") obtained as set forth above in Example 1 and natural M-CSF (designated "L929") obtained as set forth above in Example 1, were used to pretreat the cells.

The cells were then treated Keith medium (to obtain control levels of PGE$_2$), both sources of M-CSF (to demonstrate the effect of treatment with different M-CSF samples), LPS alone at a concentration of 1 μg/ml, and a combination of LPS with both sources of M-CSF, as set forth below in Table 2. The cells were analyzed for presence of PGE$_2$ produced in ng/ml/24 hr. This experiment was repeated five times.

As shown in Table 2, the level of PGE$_2$ produced was 0.07 in the control cells, was 0.19 and 0.07 in the cells that were only pretreated with M-CSF, and was 0.06 and 0.1 in the cells that were only treated with M-CSF. In the cells pretreated only with medium, treatment with LPS increased the levels to 1.27 and 1.10. In contrast, in cells that were treated with LPS and either pretreated or cotreated with M-CSF, production of PGE$_2$ was inhibited by 48%, 87–89%, or 100%. Thus, either pretreatment or cotreatment with M-CSF will decrease the production of PGE$_2$ stimulated by LPS.

TABLE 2

Pretreatment or Co-Treatment of M-CSF Reduces LPS induced PGE$_2$ Formation by Macrophages

| Pretreatment | Treatment | PGE$_2$ (ng/ml/24 h) ± S.D. | % Inhibition |
|---|---|---|---|
| Medium | Medium | 0.07 ± 0.0035 | |
| Medium | LPS (1 μg/ml) | 1.27 ± 0.09 | |
| Medium | M-CSF (L929)* | 0.06 ± 0.005 | — |
| Medium | M-CSF (rh)** | 0.1 ± 0.009 | — |
| Medium | LPS + M-CSF (L929)* | 0.7 ± 0.03 | 48 |
| Medium | LPS + M-CSF (rh)** | 0.2 ± 0.001 | 89 |
| Medium | Medium | 0.07 ± 0.003 | — |
| M-CSF (rh)** | Medium | 0.190 ± 0.009 | — |
| M-CSF (L929)* | Medium | 0.07 ± 0.004 | — |
| Medium | LPS (1 μg/ml) | 1.10 ± 0.02 | — |
| M-CSF (rh)** | LPS (1 μg/ml) | 0.2 ± 0.001 | 87 |
| M-CSF (L929)* | LPS (1 μg/ml) | 0.07 ± 0.004 | 100 |

*L929: purified natural M-CSF from L929 fibroblasts
**rh: recombinant human M-CSF-(3-153) (E. coli[3-153]M-CSF)

B. M-CSF regulates production of IL-1 inhibitor

Macrophages obtained as set forth above in Example 1 were pretreated for 24 hours with either culture medium or rh-M-CSF-(3-153), i.e., recombinant M-CSF {E. coli[3-153]M-CSF} at concentrations of 0.01, 0.03, 0.1, 0.3 and 1.0 μg/ml. Cells that were pretreated with medium were then treated with either medium (to obtain a control), 1.0 μg/ml of LPS alone, rh-M-CSF-(3-153) alone at concentrations of 1.0, 0.3, 0.01, 0.03 μg/ml, or with 1.0 μg/ml of LPS with the four concentrations of rh-M-CSF-(3-153). Cells that were pretreated with rh-M-CSF-(3-153) were treated with either medium or LPS at 1.0 μg/ml.

To assess the effect on the production of bioactive IL-1, the culture supernatant was subjected to a thymocyte assay as described above in Example 1 except that results were set forth as a stimulation index. The stimulation index refers to the cpm in the presence of ConA and macrophage conditioned medium at a given dilution/cpm in the presence of ConA only.

As indicated in Table 3, the stimulation index values for the control samples were 2.5 (for pretreatment and treatment with medium) and 1.19 to 1.67 (for pretreatment with varying concentrations of M-CSF and treatment with medium). The stimulation index value from LPS treatment Was almost ten times greater, at 20.3. In contrast, in samples pretreated with M-CSF and stimulated with LPS, the stimulation index values ranged only from 6.02 to 10.09, representing an inhibition of IL-1 bioactivity of 51 to 70%.

Similarly, in samples co-treated with varying concentrations of M-CSF, the stimulation index values ranged from 5.65 to 11.8, representing an inhibition of IL-1 bioactivity of 72 to 42%. The inhibition appeared to be concentration dependent because the greatest inhibition was observed with 1.0 μg/ml of M-CSF and the lowest inhibition with 0.03 μg/ml of M-CSF. The $EC_{50}$ (effective concentration that results in 50% inhibition) for rh-M-CSF-(3-153) was determined to be approximately 1.1 nM.

TABLE 3

Effect of recombinant M-CSF on Bioactive IL-1 Production in Response to LPS

| Pre-treatment (24 h) | Concentration | Treatment (24 h) | Concentration | Stimulation Index Over ConA control in Thymocyte Assay | % Inhibition of IL-1 Bioactivity |
|---|---|---|---|---|---|
| Medium | — | Medium | — | 2.5 | |
| Medium | — | LPS | 1 μg/ml | 20.3 | |
| Medium | — | M-CSF | 1 μg/ml | 1.01 | |
| Medium | — | LPS + M-CSF | 1 μg/ml | 5.65 | 72 |
| Medium | — | M-CSF | 0.3 μg/ml | 1.62 | |
| Medium | — | LPS + M-CSF | 1 + 0.3 μg/ml | 6.89 | 66 |
| Medium | — | M-CSF | 0.01 μg/ml | 1.61 | |
| Medium | — | LPS + M-CSF | 1 + 0.01 μg/ml | 7.78 | 60 |
| Medium | — | M-CSF | 0.03 μg/ml | 1.26 | |
| Medium | — | LPS + M-CSF | 1 + 0.03 μg/ml | 11.8 | 42 |
| M-CSF | 1 μg/ml | Medium | — | 1.19 | |
| M-CSF | 1 μg/ml | LPS | 1 μg/ml | 7.3 | 64 |
| M-CSF | 0.3 μg/ml | Medium | — | 1.67 | |
| M-CSF | 0.3 μg/ml | LPS | 1 μg/ml | 6.02 | 70 |
| M-CSF | 0.1 μg/ml | Medium | — | 1.68 | |
| M-CSF | 0.1 μg/ml | LPS | 1 μg/ml | 6.04 | 70 |
| M-CSF | 0.03 μg/ml | Medium | — | 1.43 | |
| M-CSF | 0.03 μg/ml | LPS | 1 μg/ml | 7.8 | 62 |
| M-CSF | 0.01 μg/ml | Medium | — | 1.51 | |
| M-CSF | 0.01 μg/ml | LPS | 1 μg/ml | 10.9 | 51 |

A similar experiment was conducted with varying concentrations of natural M-CSF purified from L929 cells. As set forth in Table 3a, pretreatment with M-CSF inhibited the bioactivity of IL-1 produced from macrophages in response to LPS 39 to 93%. As above, the greatest inhibition was observed with the largest concentration of M-CSF. The $EC_{50}$ for L929 M-CSF was found to be approximately 0.6 nM.

TABLE 3a

Effect of Purified L929 M-CSF on Bioactive IL-1 Production

| Pre-treatment | Concentration | Treatment | Concentration | Stimulation Index | % Inhibition |
|---|---|---|---|---|---|
| Medium | — | Medium | — | 1.21 | — |
| Medium | — | LPS | 1 μg/ml | 8.53 | — |
| L929 | 10 Ku/ml | Medium | — | 1.75 | — |
| L929 | 10 Ku/ml | LPS | 1 μg/ml | 2.43 | 93 |
| L929 | 3.3 Ku/ml | Medium | — | 1.45 | |
| L929 | 3.3 Ku/ml | LPS | 1 μg/ml | 4.21 | 62 |
| L929 | 1.1 Ku/ml | Medium | — | 1.49 | |
| L929 | 1.1 Ku/ml | LPS | 1 μg/ml | 5.97 | 39 |

These two experiments were repreated more than twelve times with various preparations of M-CSF and each experiment yielded similar results. Thus, these experiments indicate that either pretreatment or cotreatment with M-CSF decreases the bioactivity of IL-1 in response to LPS. In addition, that effect appears to be concentration dependent.

Figure 3:
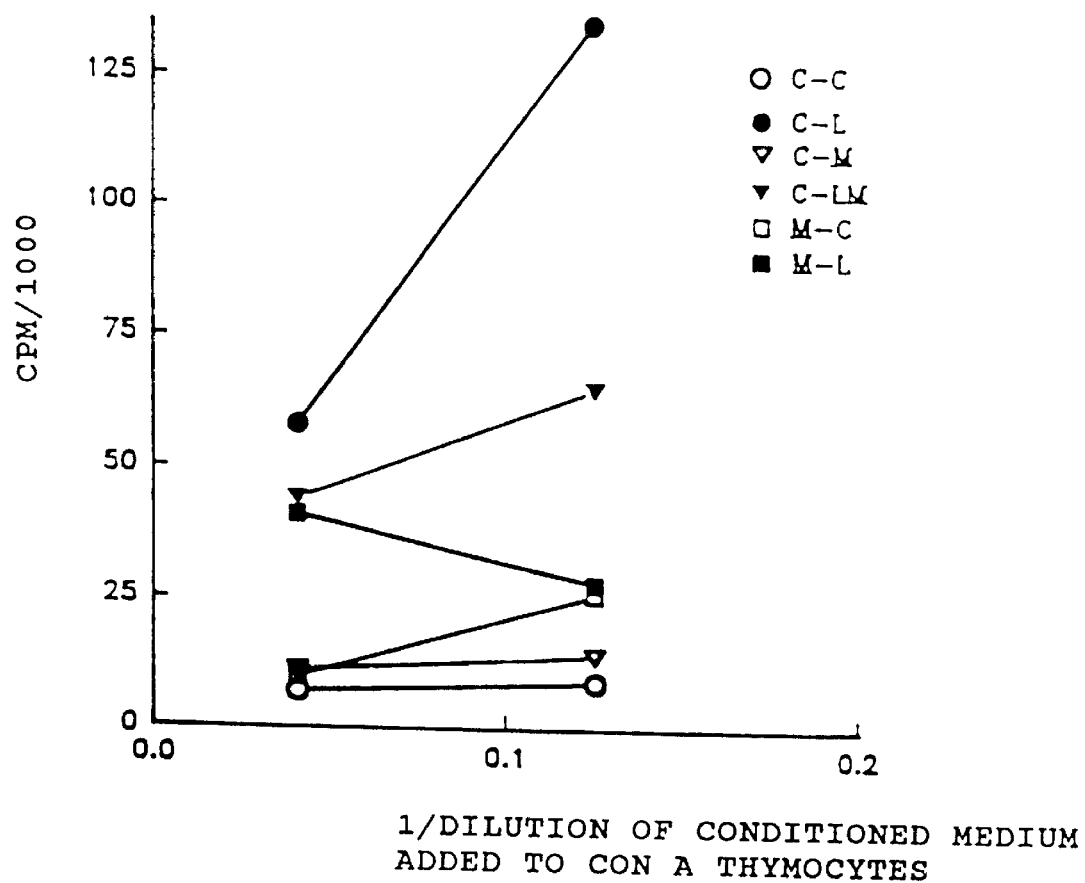
FIG. 3 is a graph that depicts the bioavailability of IL-1 produced by macrophages in the presence of M-CSF, LPS, and a combination of LPS and M-CSF.

These results are set forth graphically in FIG. 3. When the bioactivity of IL-1 (CPM/1000) is plotted against the pretreatment and treatment regimens, the greatest increase in bioactive IL-1 is seen with pretreatment with medium and treatment with LPS (C-L) as compared with pretreatment and treatment with media (C—C). A much more modest increase in bioactive IL-1 is seen With pretreatment with medium and treatment with a combination of LPS and M-CSF (C-LM). A drop in bioactive IL-1 is seen with samples pretreated with M-CSF and treated with LPS (M-L). Thus, it appears that M-CSF regulates the production of IL-1 in macrophages stimulated by LPS.

C. Potential mechanism of action of M-CSF on IL-1 bioactivity

Is set Forth above in FIGS. 1 and 2, LPS induces the expression of IL-1 (primarily IL-1α in macrophages) and as set forth in FIG. 3 and Tables 3 and 3a above, LPS also increases the production of bioactive IL-1. When cells are treated with LPS and either pretreated or cotreated with M-CSF, the level of bioactive IL-1 decreases. The expression of IL-1, however, does not appear to be affected by cotreatment with LPS and M-CSF. As set forth in FIG. 2, the combination of M-CSF and LPS exhibited a pattern in the autoradiograph of IL-1 expression that was very similar to the pattern observed with LPS alone. These observations could be explained by the M-CSF dependent stimulation of an IL-1 inhibitor which in turn decreases the bioactivity of IL-1. The production of an IL-1 inhibitor was tested by conducting an IL-1 thymocyte assay which has been supplemented by the addition of both ConA and IL-1. The addition of these two components allows an assessment of the action of an IL-1 inhibitor by providing a detectable level of bioactive IL-1 so that any decrease in the level of IL-1 can be measured.

Figure 4:
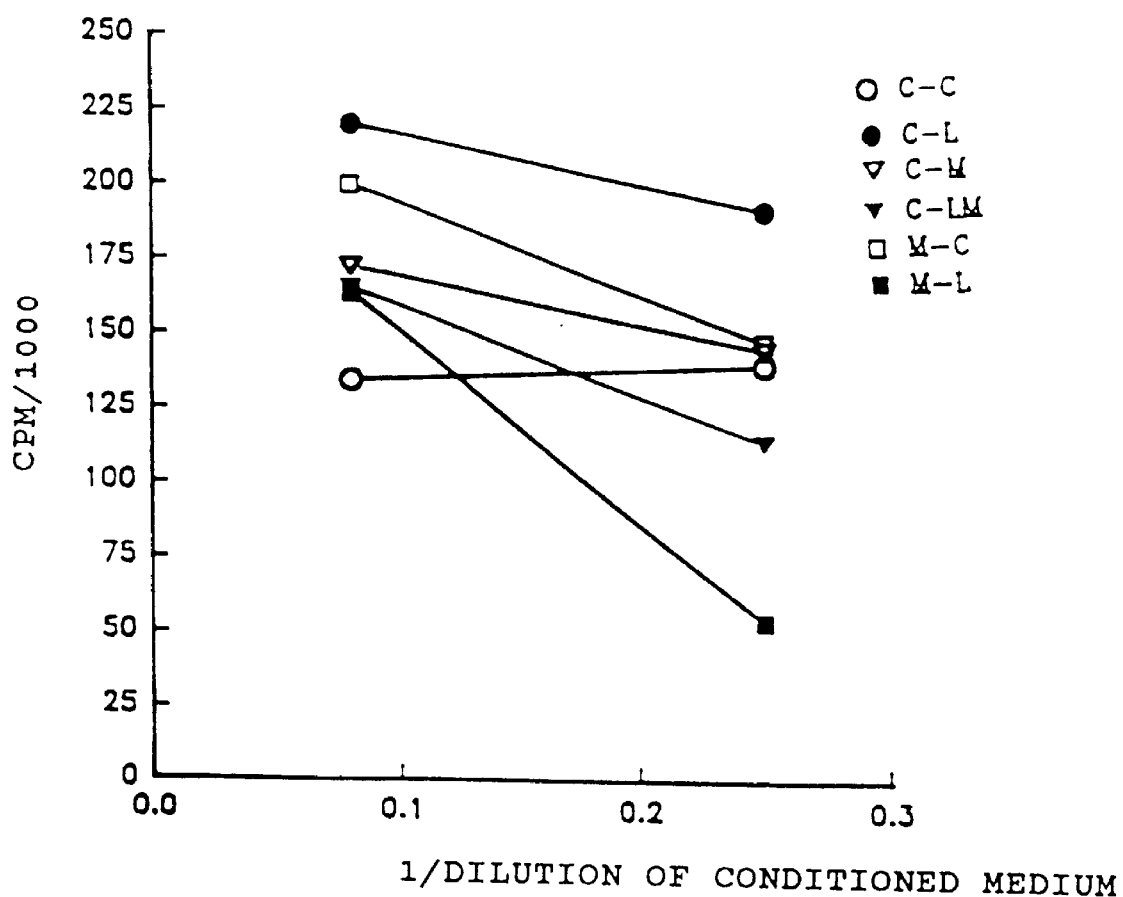
FIG. 4 is a graph that depicts the production of an IL-1 inhibitor in the presence of LPS, M-CSF, or a combination of LPS and M-CSF.

Six sets of conditioned media were added to the IL-1 thymocyte assay as set forth in FIG. 4. In the set pretreated and treated with media (C—C), the level of bioactive IL-1 remained the same. In contrast, although some decrease in bioactive IL-1 was seen with sets pretreated with media or M-CSF and treated with M-CSF or LPS or a combination of M-CSF and LPS, the only real decrease in IL-1 bioactivity was seen in the set pretreated with M-CSF and treated with LPS (M-L). Thus, this study implicates M-CSF in the production of an inhibitor to IL-1.

To determine whether the inhibitor was specific to IL-1, a similar experiment was conducted with IL-6. Six sets of macrophages were pretreated with either media (C) or M-CSF (M) and treated with either media, M-CSF, LPS, or a combination of M-CSF and LPS as set forth in FIG. 5. The activity of IL-6 was assessed using the IL-6 B-9 assay set forth above.

Figure 5:
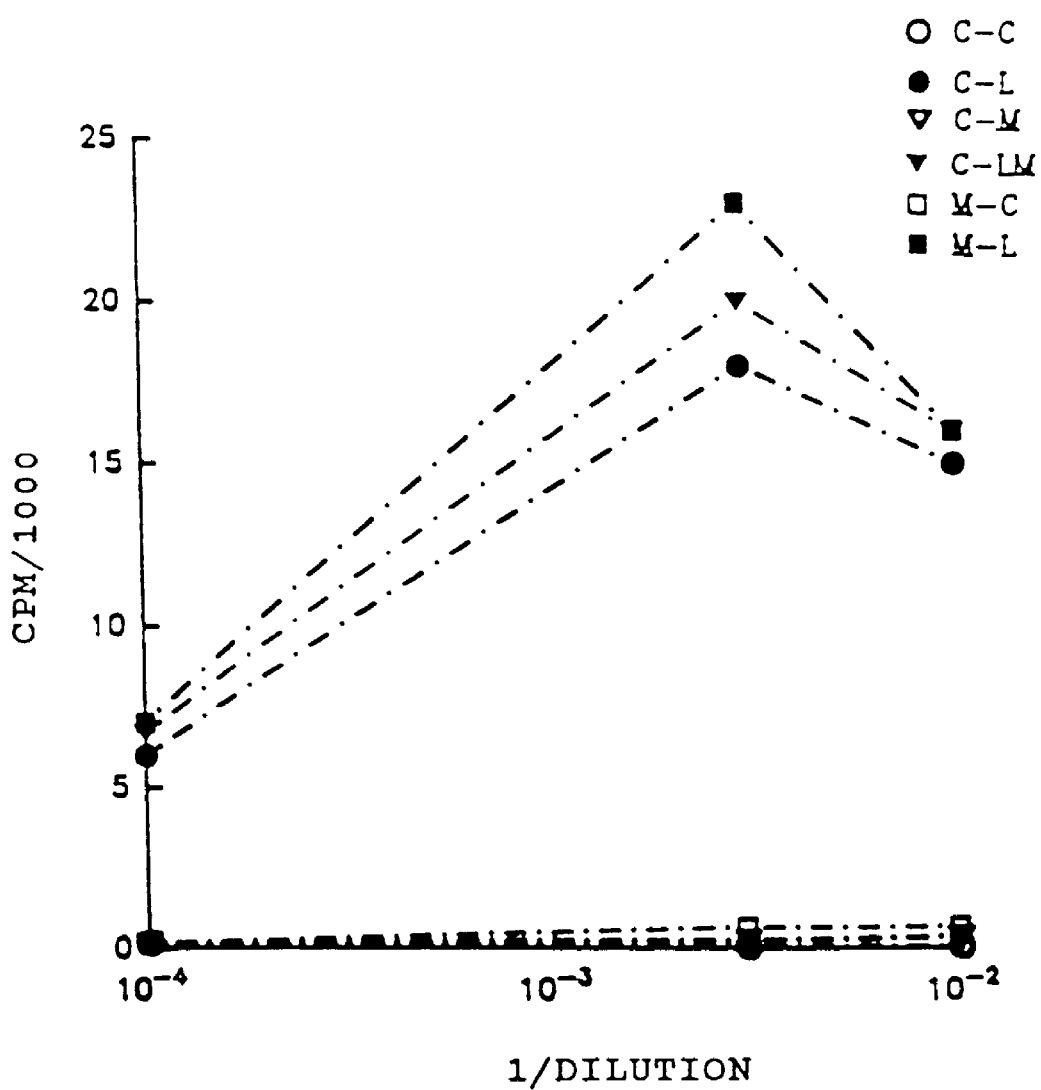
FIG. 5 is a graph that depicts the lack of production of an IL-6 inhibitor in the presence of LPS, M-CSF, or a combination of LPS and M-CSF.
Figure 6:
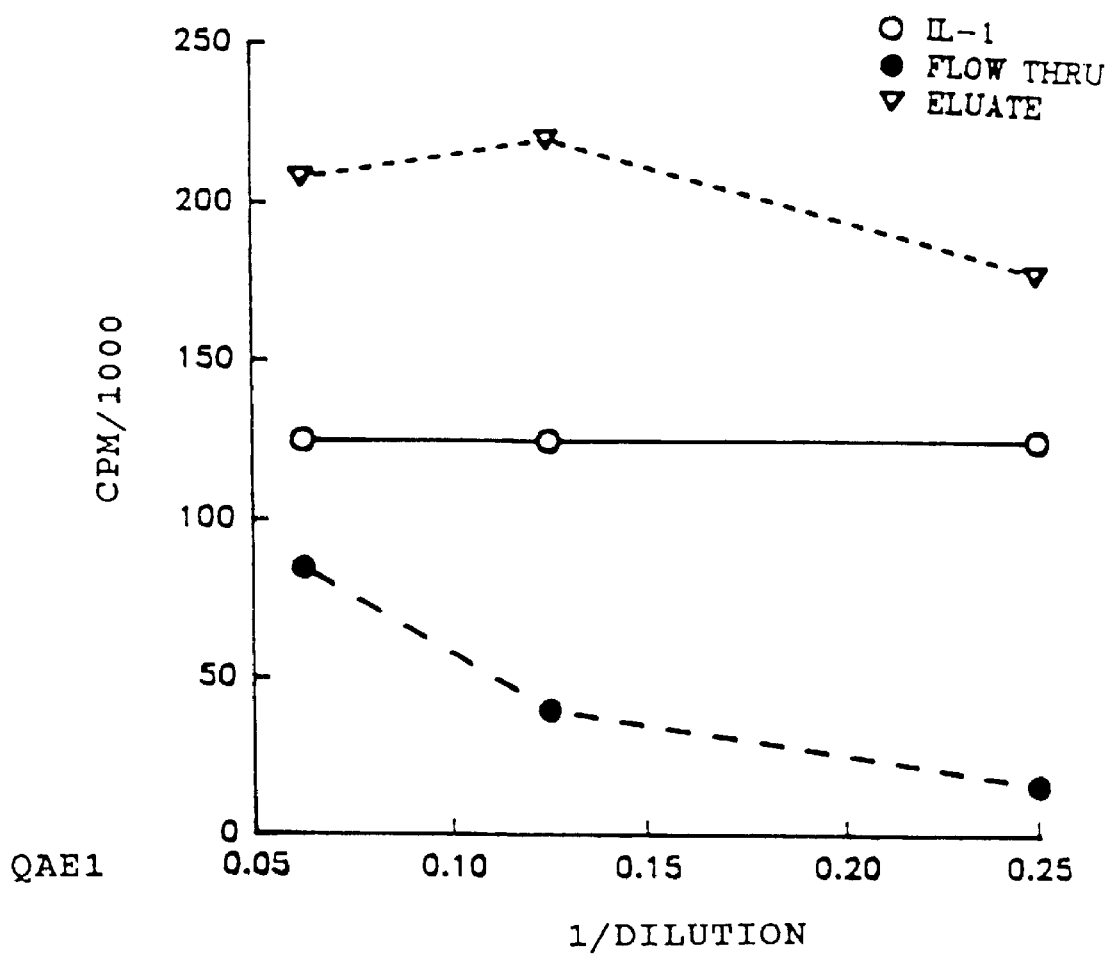
FIG. 6 is a graph that depicts the separation of an IL-1 inhibitor from IL-1 in a QAE-52 column.
Figure 7:
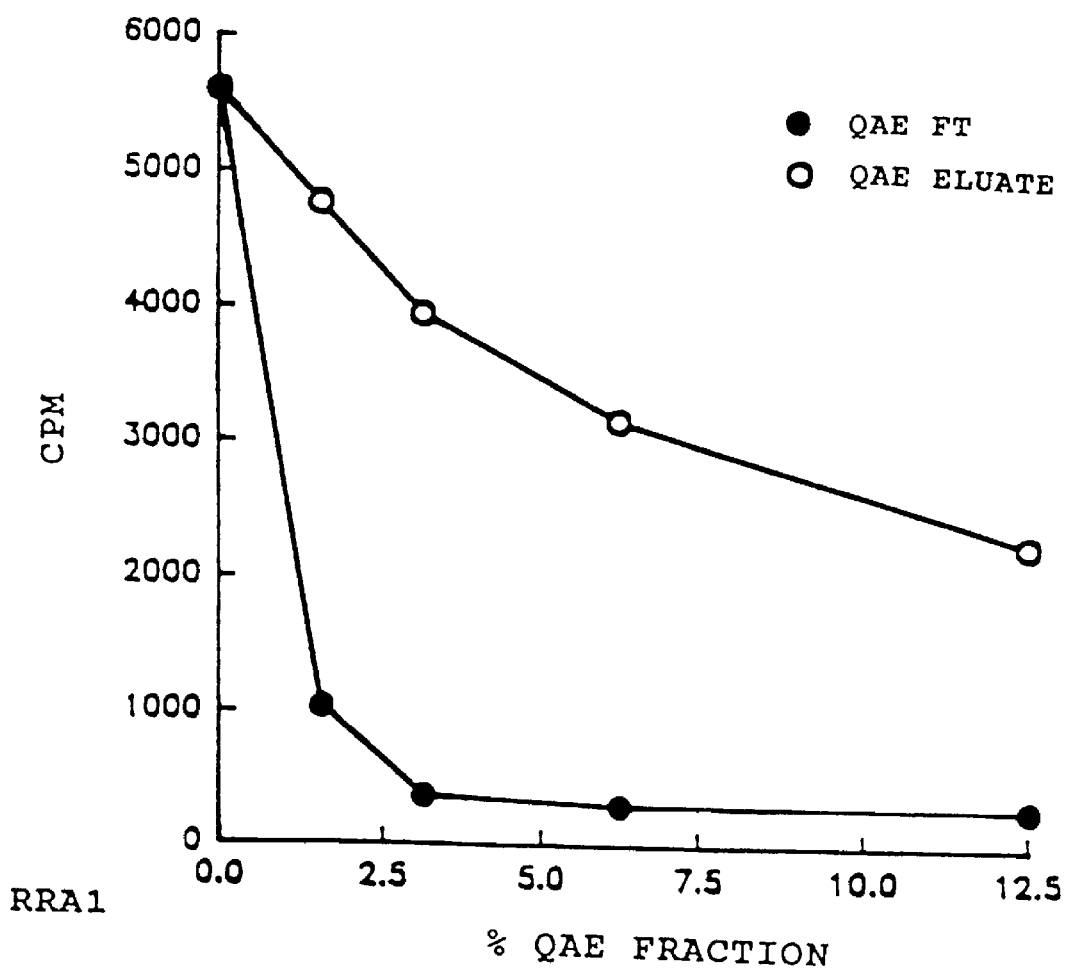
FIG. 7 is a graph that depicts the ability of IL-1 and the IL-1 inhibitor to bind to the IL-1 receptor.

As demonstrated in FIG. 5, a similar pattern of IL-6 bioactivity was observed in cells pretreated with media and treated with LPS, in cells pretreated with media and treated with a combination of LPS and M-CSF, and in cells pretreated with M-CSF and treated with LPS. The inhibitor stimulated by M-CSF appeared to have no effect on IL-6 activity. This pattern is quite different from the pattern observed with IL-1 production in FIG. 4 in which a dramatic decrease in IL-1 was seen in culture supernatant from cells pretreated with M-CSF and treated with LPS. Thus, this study indicates that the IL-1 inhibitor is specific to IL-1 and that, under the same conditions, M-CSF does not regulate the production of an inhibitor specific to IL-6.

EXAMPLE 3

Injection of M-CSF in vivo results in reduction of IL-1 bioactivity produced in response to LPS Eight inbred female pathogen-free C57B1/6 mice (Charles River Breeding Laboratories, Wilmington, Mass.) were injected intraperitoneally with 1.0 ml of sterile Brewer's thioglycollate (TG) at time 0 and divided into four groups. As set forth in Table 4 below, at 72 hours, the mice in group 1, the control group, and group 2 were pretreated with 0.2 ml phosphate buffered saline (hereinafter "PBS") and the mice in groups 3 and 4 were pretreated with PBS containing M-CSF-(3-153) at 4 μg/mouse. At 90 hours, the control group 1 was treated with PBS, group 2 was treated with PBS containing 50 μg/mouse of LPS (to show the effect of LPS treatment), group 3 was treated with PBS (to show the effect of M-CSF pretreatment alone), and group 4 was treated with PBS containing 50 μg/mouse of LPS (to show the effect of M-CSF pretreatment on LPS treatment).

Eight hours later, the mice were sacrificed and their peritoneal cells collected as set forth above in Example 1. Cells at $1 \times 10^6$ cells/well were plated in Costar plates and treated with conditioned medium.

Twenty hours later, the conditioned media was collected and titrated into the IL-1 bioassay set forth above (thymocyte pulsed with ConA). Results are expressed as a mean cpm of triplicate wells.

The percent inhibition of IL-1 bioactivity was determined as follows:

$$\frac{(CPM \text{ group } 2 - CPM \text{ group } 1) - (CPM \text{ group } 4 - CPM \text{ group } 1)}{CPM \text{ group } 2 - CPM \text{ group } 1} \times 100$$

As set forth below in Table 4, at 1/4 dilution of conditioned media, treatment with LPS (group 2) yielded 13103 CPM of bioactive IL-1 while pretreatment with M-CSF (group 4) yielded 5050 CPM. At 1/12 dilution, treatment with LPS (group 2) yielded 5385 CPM compared to 2592 CPM obtained with pretreatment with M-CSF (group 4). Thus, at both 1/12 and 1/4 dilutions of the conditioned media, pretreatment with M-CSF inhibited the bioactivity of IL-1 produced in response to LPS by 69.9%, indicated that M-CSF can inhibit IL-1 bioactivity both in vitro and in vivo.

TABLE 4

Injection of M-CSF In Vivo Results in Reduction of IL-1 Bioactivity Produced in Response to LPS

| Group | Treatment of Mice in Vivo | Dilution of Conditioned Media | | % Inhibition |
|---|---|---|---|---|
| | | 1/4 | 1/12 | |
| 1 | TG (0 hrs) → PBS (72 hrs) → PBS (90 hrs) | 1583 | 1353 | — |
| 2 | TG (0 hrs) → PBS (72 hrs) → LPS (90 hrs) | 13103 | 5385 | — |
| 3 | TG (0 hrs) → M-CSF (72 hrs) → PBS (90 hrs) | 1301 | 1308 | — |
| 4 | TG (0 hrs) → M-CSF (72 hrs) → LPS (90 hrs) | 5050 | 2592 | 69.9 |

EXAMPLE 4

Separation and assessment of the IL-1 inhibitor

A. Separation and Characterization of the IL-1 inhibitor

To further assess the IL-1 inhibitor, the conditioned media treated with M-CSF and LPS was subjected to a QAE-52 column to separate the IL-1 from the IL-inhibitor. As an anion exchanger, QAE-52 at pH 7.4 has the capability to separate IL-1α, which has a pI of 5.5, from the IL-1 inhibitor.

To separate the IL-1 inhibitor, $3.0 \times 10^8$ peritoneal exudate cells were cultured in 100 mm tissue culture dishes at a cell density of $2.3 \times 10^5/cm^2$ (approximately $1.8 \times 10^7$ cells/plate) in complete medium. After 2.0 hours incubation, the plates were washed twice with complete medium and 5.0 ml of M-CSF-(3-153) (1.0 μg/ml) were added per plate and incubated for 20 hours. Following this pretreatment step, the fluid was aspirated, plates were washed twice, and 5.0 ml of RPMI 1640 containing 0.5 mg/ml of bovine serum albumin and 1.0 pg/ml of LPS were added per plate. The plates were cultured for 40 hours and the conditioned medium was collected, centrifuged at 1000×g for 15 min. at 4° C. The resulting pellet was diluted with an equal volume of ice cold 20 mM HEPES buffer (pH 7.4). The material was then loaded onto a 1.5×10 cm$^2$ column packed with quaternary ammonium cellulose (QAE-52, Whatman).

The sample that did not attach to the QAE-52 flowed through the column and was collected and designated "flow thru". The sample that did attach to the QAE-52 was released in the presence of 1 M NaCl and was collected and designated "eluate". Both flow thru and eluate fractions were diafiltered and concentrated to the same volume in an Amicon chamber over a membrane with a 10 kd cut-off point.

The flow thru and eluate samples were subjected to the IL-1 thymocyte assay, the IL-1 radioreceptor assay, a TNF bioassay and an IL-2 proliferation assay.

1. IL-1 thymocyte assay

The flow thru and eluate samples were assayed with the IL-1 thymocyte assay set forth above to determine levels of bioactive IL-1 as compared to the activity of a sample of IL-1 introduced to the assay. The results are set forth in FIG. 6.

The eluate exhibited IL-1 activity even greater than that of the IL-1 sample since the thymocytes were supplemented with submaximal dose of IL-1. In contrast, the flow thru exhibited a dramatic decrease in IL-1 activity. This indicated that the eluate, which exhibited IL-1 activity, contained IL-1 and perhaps IL-6 and that the flow thru, which decreased IL-1 activity, contained the IL-1 inhibitor.

2. The IL-1 radioreceptor assay

Both the flow thru and eluate samples were assayed with the IL-1 radioreceptor assay set forth in Example 1. As set forth in FIG. 7, both fractions were able to displace $^{125}$IL-1α bound to EL-4.6 cells although the flow thru exhibited greater displacement than did the eluate. This suggested that both the IL-1 and the IL-1 inhibitor bound to the IL-1 receptor.

3. The TNF assay

To determine the specificity of the IL-1 inhibitor present in the flow thru of the QAE-52, the flow thru sample was tested in the TNF bioassay described by Nedwin, G. E., et al., "Effect of interleukin 2, interferon gamma, and mitogens on the production of tumor necrosis factors α and β", *J. Immunology* 135: 2492 (1985). In this assay, 5.0×10$^4$ cells per well of L929 fibroblasts were plated in flat-bottomed microtiter plates in the presence of 1.0 U/ml of actinomycin D. Diluted samples from the QAE-52 flow thru were added with or without serial dilutions of TNF-α (obtained from Amgen) to a final volume of 0.2 ml. Following 24 hours of incubation at 37° C., under 6.0% $CO_2$, the monolayers were washed. Cell lysis was determined by the addition of a solution of 0.5% (w/v) crystal violet in a mixture of methanol and water (1:4 (v/v)) and quantitated by the measurement of absorbance at 570 nm on a Titertek multiscan ELISA reader.

Figure 8:
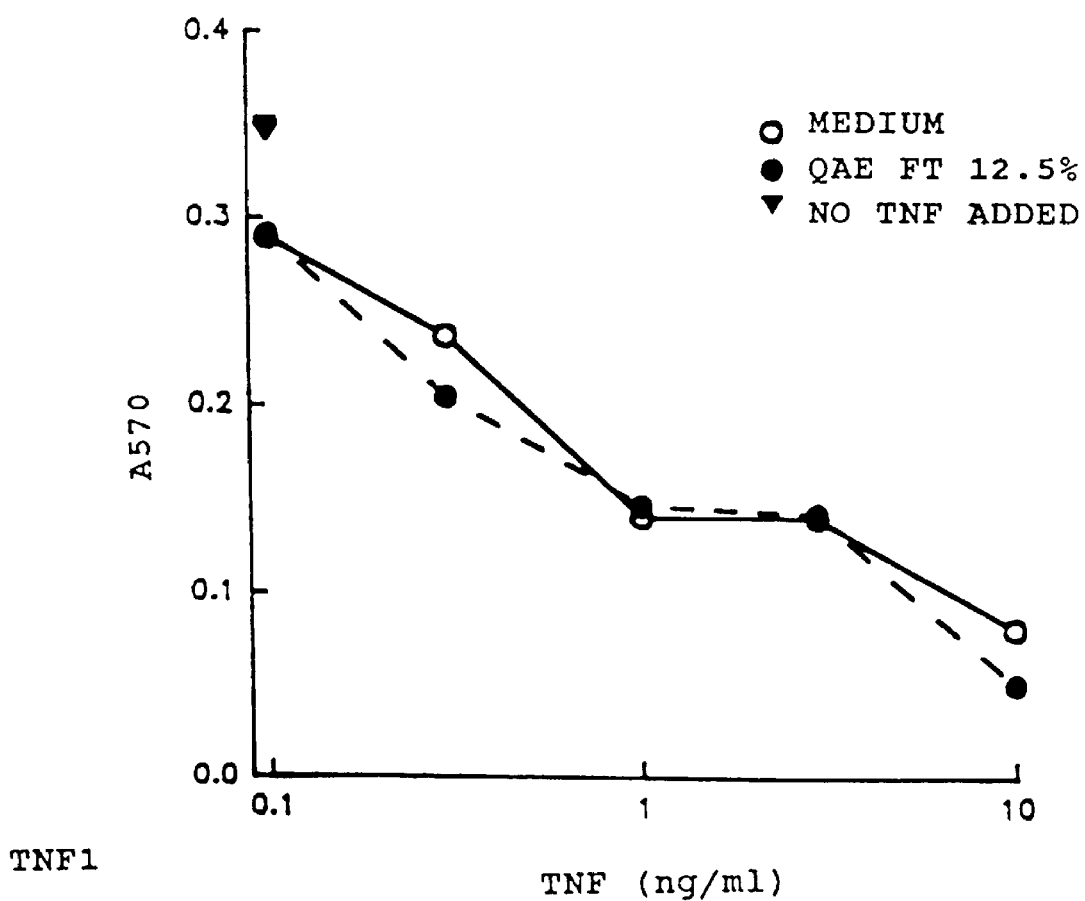
FIG. 8 is a graph that depicts the effect of the IL-1 inhibitor on the action of TNF.
Figure 9:
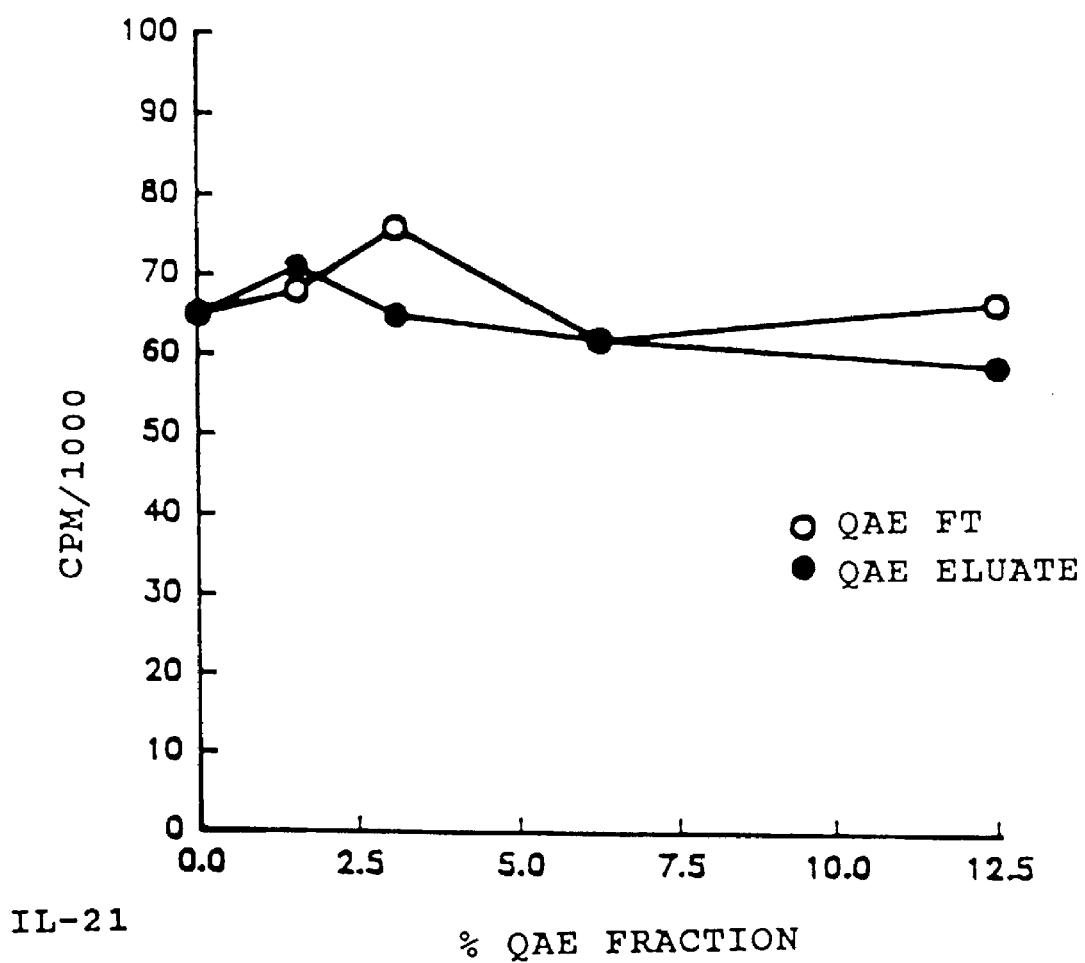
FIG. 9 is a graph that depicts the effect of the IL-1 inhibitor and IL-1 on the response of T cells to IL-2.

As shown in FIG. 8, the curves corresponding to the medium and the 12.5% flow thru exhibit virtually identical patterns, indicating that the QAE-52 flow thru neither inhibits nor stimulates the ability of TNF-α to destroy L929 indicator cells. Thus, this study indicates that the IL-1 inhibitor is specific to IL-1 and has no effect on TNF activity.

4. The IL-2 bioassay

To determine the specificity of the IL-1 inhibitor in the QAE flow thru, both the QAE flow thru and the QAE eluate were tested in a bioassay for IL-2 described in Gillis, S, et al., "T cell growth factor parameters of production and a quantitative microassay for activity", *J. Immunol.* 120: 2027 (1978). As set forth in FIG. 9, neither the flow thru nor the eluate were able to efect the activity of IL-2. Both samples exhibited an almost straight horizontal line, indicating no promotion or inhibition of IL-2 proliferation.

B. Purification of the IL-1 inhibitor

After determining that the IL-1 inhibitor could resist acid and heat but not trypsinization, the IL-1 inhibitor was further purified on reverse phase-HPLC using acetonitrile as an eluant for C-4 column.

In this purification, the material in the flow thru collection was lyophilized, resuspended in 10% (v/v) acetonitrile/0.1% (v/v) trifluoroacetic acid/water and injected into a C-4 column (The Nest Group) connected to a reversed phase HPLC. An acetonitrile gradient (25%–50% (v/v) over 60 min., with a flow rate of 1.0 ml/min.) was applied and fractions were collected, lyophilized, and resuspended in the corresponding buffer. The samples were tested in the IL-1 thymocyte bioassay described above, the IL-1 receptor assay described in Example 1 and in the thymocyte assay described in Example 2.

Figure 10:
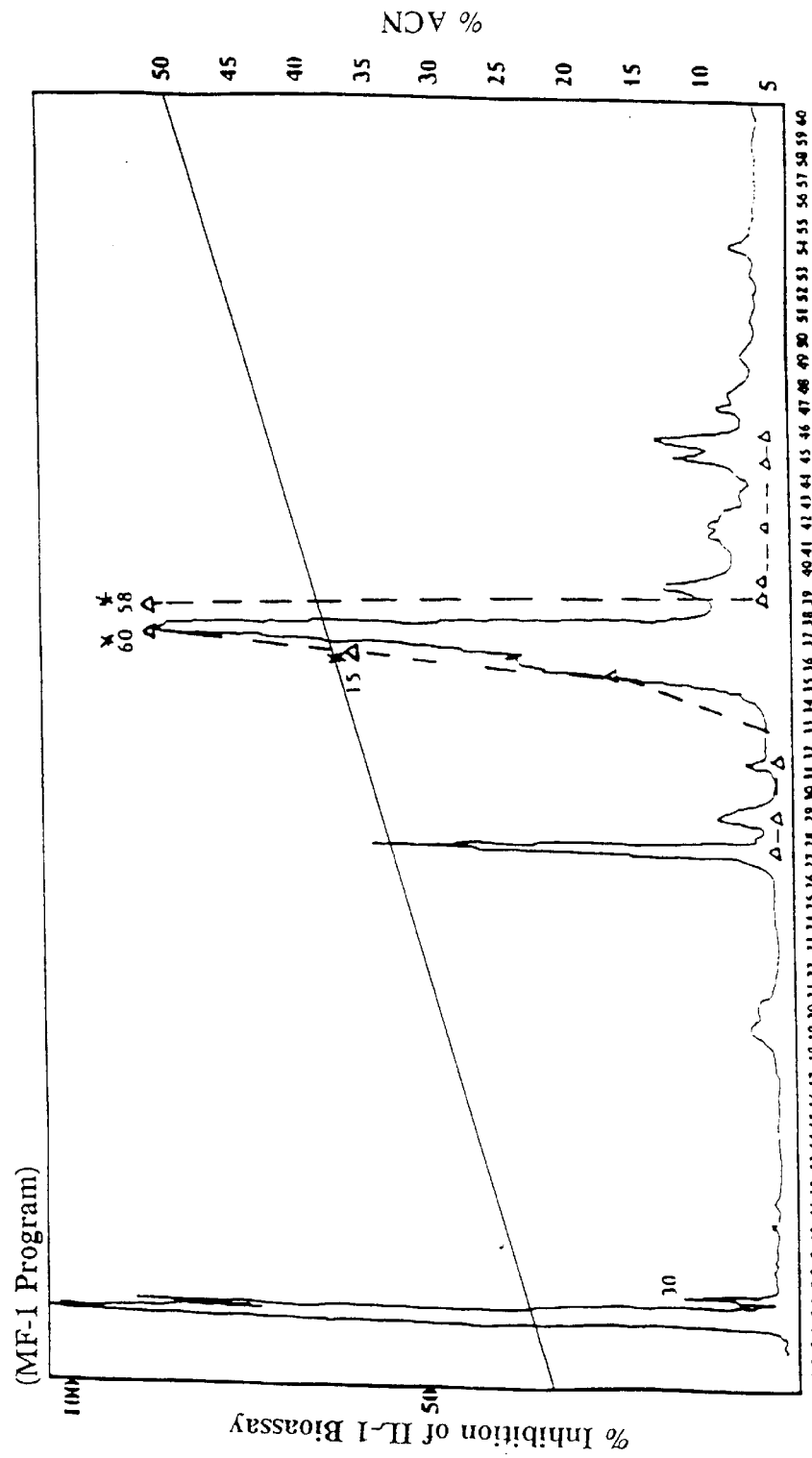
FIG. 10 is a graph that depicts the purification of an IL-1 inhibitor on reverse phase HPLC C-4 column and the activity of the IL-1 inhibitor in terms of IL-1 bioassay, binding with the IL-1 receptor and inhibition of bioactive IL-1.

As shown in FIG. 10, the peak activity for IL-1 inhibition as determined by IL-1 bioassay (the solid lines) is found in fractions 13–38. Those fractions correspond to approximately 37% acetonitrile. Additional tests with the IL-1 radioreceptor binding assay showed that only these fractions were able to displace IL-1 (the * line). Similarly, in the IL-1 thymocyte assay stimulated with ConA and IL-1 as set forth above, only these fractions were able to inhibit thymocytes proliferation (the triangles lines). Thus, the IL-1 inhibitor stimulated by M-CSF can be separated on reverse phase HPLC.

Hereinafter, the anti-allergic composition of the invention will be described in greater detail with reference to Reference Examples that show the preparation of the M-CSF derivatives of the invention and Examples that show their anti-allergic properties.

Herein, the human M-CSF derivatives produced are defined as follows. That is to say, the M-CSF produced by an expression vector coding for the amino acid sequence of Val at position 3 to Thr at position 153 of the amino acid sequence defined by the formula (1) with *E. coli* as the host is designated "*E. coli*[3-153]M-CSF" and, similarly, the one produced by an expression vector coding for the amino acid sequence of Val at position 3 to Pro at position 214 is designated "*E. coli*[3-214]M-CSF".

Further, the M-CSF produced by an expression vector coding for the amino acid sequence of Ser at position 4 to Thr at position 153 with *E. coli* as the host is designated "*E. coli*[4-153]M-CSF", and similarly one produced by an expression vector coding for the amino acid sequence of Ser at position 4 to Pro at position 214 is designated "*E. coli*[4-214]M-CSF".

The M-CSF derivative obtained in Reference Example 1 as produced by an expression vector coding for a signal peptide comprising a sequence of 32 amino acids and the mature human M-CSF protein comprising a sequence of 522 amino acids with CHO cells as the host is designated "CHO[-32-522]M-CSF".

The samples obtained in the examples were assayed for CSF activity by the following method.

Method of determining CSF activity

Fetal calf serum (FCS, 20 ml), 30 ml of α-medium and 20 ml of α-medium of 2-fold concentration are mixed together, and the solution is maintained at 37° C. A 23.3-ml portion of the solution is admixed with 10 ml of 1% solution of agar (product of Difco Laboratories) already maintained at 50° C. and the mixture is maintained at 37° C.

Separately, bone marrow cells (BMC) collected from the femur of a BALB/c mouse are washed twice with Hanks' solution and then suspended in α-medium to a concentration of $10^7$ cells/ml, and 1 ml of the suspension is added to the agar medium maintained at 37° C. The mixture is thoroughly stirred and then maintained at 37° C. A 0.5-ml portion of the mixture is placed in each well (Tissue Culture Cluster 12, product of Costar Corporation) already containing 50 μl of a test sample, and the resulting mixture is quickly stirred and then allowed to stand at room temperature. On solidification of the agar in each well, the wells are placed in a carbon dioxide gas incubator and further incubated at 37° C. for 7 days.

The number of colonies thus produced is counted under a stereoscopic microscope to provide an index for the CSF activity. The CSF activity in units (U/ml) is the value calculated from the above-mentioned colony count according to the following formula (a).

CSF activity in units (U/ml)=(colony count)×(dilution factor)÷1.(a)

When observed morphologically and enzymochemically, the colonies that formed in the above were mostly macrophage colonies.

Reference Example 1
Preparation of CHO[-32-522]M-CSF

Using the culture supernatant of the CHO cell clone No. 2, 3-8 [Unexamined Japanese Patent Publication HEI 1-104176] microcarrier-cultured in OPTI-MEM (product of Gibco Laboratories) containing 1% FCS, the desired homogeneous CHO[-32-522]M-CSF was obtained by the following purification procedure. In the following procedure, the desired protein was detected by the Western blotting method. Said Western blotting was performed using Bio-Rad Laboratories Transblot cell. The nitrocellulose membrane after transfer was blocked with PBS containing 1% skim milk, then reacted with a rabbit antiserum against M-CSF and further reacted with peroxidase-labeled goat anti-rabbit antibody (product of Bio-Rad Laboratories). For detecting the M-CSF band, the thus-obtained nitrocellulose membrane was reacted with a solution of the chromogenic substrate 4-chloro-1-naphthol.

(1) ConA-Sepharose chromatography

The above-mentioned CHO cell culture supernatant (69.3 l) was concentrated by ultrafiltration, and a 650-ml portion of the concentrate (842 ml) was used as the starting material and subjected to fractionation with ammonium sulfate. The precipitate fractions obtained by 35%–65% saturation with ammonium sulfate were dissolved in distilled water (1,120 ml) to give a sample solution.

Separately, a column (5×25 cm) packed with about 500 ml of ConA-Sepharose gel was equilibrated with 20 mM sodium phosphate buffer (pH 7.4) containing 0.15M NaCl, and the above sample solution was applied to the column. After thorough washing with the same buffer, elution was carried out with the same buffer containing 0.5M methyl α-D-mannoside. The whole eluate was concentrated by ultrafiltration using a YM-10 membrane, then buffer was exchanged to 20 mM sodium phosphate buffer (pH 7.4), and the resulting solution was subjected, in 7 aliquots, to anion exchange high-performance liquid chromatography under the following conditions.

(2) Anion exchange high-performance liquid chromatography

Column: TSKgel DEAE-5PW (21.5 mm I.D.×15 cm, product of Tosoh Corporation)
Eluent A: 40 mM Sodium phosphate buffer (pH 7.4)
Eluent B: 40 mM Sodium phosphate buffer (pH 7.4) containing 1.0M NaCl
Flow rate: 3.0 ml/min.
Fraction volume: 6 ml/tube/2 min.

| Concentration gradient: | Time (min) | B % |
|---|---|---|
| | 0 | 0 |
| | 10 | 0 |
| | 20 | 10 |
| | 95 | 30 |
| | 100 | 100 |
| | 110 | 100 |
| | 115 | 0 |
| | 130 | 0 |

As a result of the above elution, the desired M-CSF was eluted into fractions Nos. 26–38 (0.18 to 0.25M NaCl). Said active fractions were pooled, concentrated by ultrafiltration (using a YM-10 membrane) and purified as follows.

(3) Gel filtration high-performance liquid chromatography

The concentrated sample obtained by the above procedure (2) was subjected, in 5 aliquots, to gel filtration high-performance liquid chromatography under the following conditions.

Column: TSKgel G3000SWG (21.5 mm I.D.×60 cm, product of Tosoh Corporation)
Eluent: 50 mM sodium phosphate buffer (pH 7.4) containing 0.3M NaCl
Flow rate: 3.0 ml/min.
Fraction volume: 6 ml/tube/2 min.

As a result of the above gel filtration high-performance liquid chromatography, M-CSF was detected in fractions Nos. 20–27, of which fractions Nos. 24–27 were pooled, concentrated by ultrafiltration and subjected to the following purification procedure.

(4) TSKgel Ether-5PW high-performance liquid chromatography

The concentrated sample (12 ml) obtained by the above procedure (3) was purified, in 8 aliquots, under the following conditions.

Prior to injection into the column, the above-mentioned concentrate was admixed with 80% ammonium sulfate-saturated 20 mM sodium phosphate buffer (pH 7.4) and then subjected to chromatography.

Column: TSKgel Ether-5PW (7.5 mm I.D.×75 mm, product of Tosoh Corporation)
Eluent A: 20 mM Sodium phosphate buffer (pH 7.4)
Eluent B: 40% Ammonium sulfate-saturated 20 mM sodium phosphate (pH 7.4)
Flow rate: 1.0 ml/min.
Fraction volume: 2 ml/tube/2 min.

| Concentration gradient: | Time (min) | B % |
|---|---|---|
| | 0 | 100 |
| | 5 | 100 |
| | 65 | 0 |
| | 80 | 0 |
| | 85 | 100 |
| | 100 | 100 |

As a result of the above chromatography M-CSF was detected in fractions Nos. 15–18 (22%–17% saturated ammonium sulfate concentrations). Fractions having the same fraction number were respectively pooled and each pool was subjected, in 3 or 4 aliquots, to reversed-phase high-performance liquid chromatography.
(5) TSKgel Phenyl-5PWRP reversed-phase high-performance liquid chromatography
Column: TSKgel Phenyl-5PWRP (7.5 mm I.D.×75 mm, product of Tosoh Corporation)
Eluent A: 0.1% TFA
Eluent B: n-Propanol: 1% TFA (9:1)
Flow rate: 0.8 ml/min.
Fraction volume: 1.6 ml/tube/2 min.

| Concentration gradient: | Time (min) | B % |
|---|---|---|
| | 0 | 0 |
| | 5 | 0 |
| | 10 | 25 |
| | 50 | 45 |
| | 60 | 100 |
| | 70 | 100 |
| | 75 | 0 |
| | 95 | 0 |

As a result of the above chromatography, M-CSF was detected in two consecutive fractions out of fractions Nos. 5–8 (32%–34% n-propanol), although the fraction numbers of the two varied a little depending on the sample and experiment.

The fractionation was carried out using tubes already containing 200 μM disodium phosphate per tube. The M-CSF fractions were concentrated to dryness by centrifugation tube by tube on a concentrator (product of Tomy Seiko Co., Ltd.) and dissolved in 500 μl per tube of distilled water and the resulting solutions were subjected to experimentation.

(6) SDS-PAGE of CHO[-32-522]M-CSF

According to the method of Laemmli [Laemmli, U. K., Nature, 277, 680 (1970)], the CHO[-32-522]M-CSF obtained by the above procedure (5) was admixed with Laemmli's sample buffer [either of the one containing 2-mercaptoethanol (2-ME$^+$) and the one free of it (2-ME$^{31}$)], the respective mixtures were heat-treated at 95° C. for 10 minutes and then subjected to SDS-PAGE using mini slab gels (gel concentration 12%). Prestained markers (product of Bio-Rad Laboratories) were used as molecular weight markers. For staining, Silver Stain (product of Wako Pure Chemical Industries) was used.

As a result, under non-reducing conditions (state of 2-ME$^-$), a smeared band was detected over the molecular weight range of 62,000–115,000 with a main component at a molecular weight of about 85,000 and, under reducing conditions (state of 2-ME$^+$), a smear band was detected over 39,000–46,000 with a main component at 43,000.

(7) N-Terminal region amino acid sequence of CHO[-32-522]M-CSF

The N-terminal region amino acid sequence of the CHO [-32-522]M-CSF obtained by the above procedure (5) was determined using a gaseous phase sequencer (product of Applied Biosystems).

As a result, the sequence of the N-terminal 10 amino acids was confirmed to be as follows. The amino acid (X') in cycle 7 could not be identified but was estimated as Cys based on the gene structure.

Glu-Glu-Val-Ser-Glu-Tyr-X'-Ser-His-Met-

Reference Example 2

[1] Preparation of plasmid ptrpIL-2X-M-CSF101

The plasmid pcDM-CSF11-185 [prepared from the plasmid pcDM-CSF11 containing the M-CSF gene (λcM11 cDNA, about 2.5 kb) (cf. Unexamined Japanese Patent Publication HEI 1-104176)] was digested with the restriction enzymes ScaI and BamHI, and a ScaI-BamHI DNA fragment (about 450 bp) was isolated and purified by agarose gel electrophoresis. Then, the synthetic linker (A) shown below was ligated to the ScaI cleavage site of the above-obtained DNA fragment using T4 DNA ligase to give an XbaI-BamHI DNA fragment (about 480 bp) having an XbaI (restriction enzyme) cleavage site on the ScaI cleavage end side.

Synthetic linker (A):

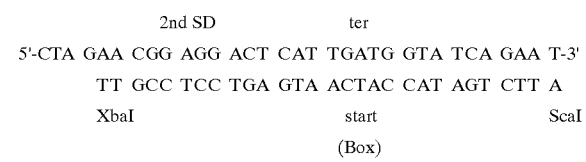

(Box)

The thus-obtained DNA fragment was inserted into the human IL-2 expression plasmid ptrpIL-2D8Δ (Unexamined Japanese Patent Publication SHO 63-12958) between the XbaI and BamHI cleavage sites, whereby the desired plasmid ptrpIL-2X-M-CSF101 was obtained.

A transformant obtained by transforming *Escherichia coli* HB101 with said plasmid has been deposited, under the name of *Escherichia coli* HB101/ptrpIL-2X-M-CSF101, in the Fermentation Research Institute, Agency of Industrial Science and Technology with the deposition number of FERM BP-2226 (*E. coli*[3-153] FERM BP-2226] since Dec. 26, 1988.

[2] Isolation and purification of *E. coli*[3-153] M-CSF (1) Preparation of M-CSF fraction from *Escherichia coli*

To 1.5 g (wet weight) of an *E. coli* strain SG21058 harboring the plasmid ptrpIL-2X-M-CSF101 obtained by the above procedure [1] was added 50 ml of 50 mM Tris-hydrochloride buffer (pH 7.0) containing 0.5M sucrose, and the mixture was thoroughly stirred. Then, 6 ml of 2 mg/ml lysozyme was added, 4 ml of 0.14M EDTA was further added and, after 15 minutes of stirring at 4° C., the mixture was centrifuged at 10,000 revolutions/minute for 20 minutes.

The supernatant was discarded, and the pellet was washed with the same buffer (50 mM Tris-hydrochloride containing 0.5M sucrose, pH 7.0) and subjected to centrifugation, which was carried out similarly at 10,000 revolutions/minute for 20 minutes and gave spheroplasts as a pellet. The pellet was suspended in 50 ml of 50 mM Tris-hydrochloride (pH 7.0) and the suspension was subjected to sonication at 20 KHz for 10 minutes and then centrifuged at 10,000 revolutions/minute for 20 minutes. The pellet was washed with the same buffer (50 mM Tris-hydrochloride, pH 7.0) and again centrifuged under the same conditions to give an M-CSF fraction as a pellet.

(2) Refolding of M-CSF from M-CSF fraction

To the M-CSF fraction obtained by the above procedure (1) was added 100 ml of 50 mM Tris-hydrochloride (pH 7.0) containing 7.0M guanidine hydrochloride, and the mixture was solubilized by agitating with a stirrer at 4° C. for 1 hour. This solution was slowly added dropwise into a beaker already containing 300 ml of 10 mM Tris-hydrochloride (pH 8.5) (agitated with stirrer) and, after completion of the dropping, the mixture was thoroughly dialyzed against 10 mM Tris-hydrochloride (pH 8.5) at 4° C. and then centrifuged at 10,000 revolutions/minute for 20 minutes. The precipitate was discarded and the supernatant was recovered.

The refolded M-CSF is present in the thus-obtained supernatant.

(3) Purification of M-CSF

The M-CSF obtained in the above (2) was purified as follows.

(3-1) Gel filtration high-performance liquid chromatography

The supernatant obtained by the above procedure (2) was concentrated with an ultrafiltration apparatus of (product of Amicon; membrane: YM-10 membrane, product of Amicon), and the concentrate was passed through a 0.45 μm Millipore filter and then subjected to gel filtration high-performance liquid chromatography under the following conditions.

Column: TSKgel G 3000SW (60 cm×21.5 mm I.D., product of Tosoh Corporation)
Eluent: 50 mM sodium phosphate buffer (pH 6.8) containing 0.3M NaCl
Flow rate: 3.0 ml/min.
Fraction volume: 6 ml/tube/2 min.

In the above procedure, judging from the elution positions of standard proteins for gel filtration HPLC (product of Oriental Yeast Co., Ltd.), namely glutamate dehydrogenase (molecular weight 290,000), lactate dehydrogenase (molecular weight 142,000), enolase (molecular weight 67,000) and adenylate kinase (molecular weight 32,000), the molecular weight of M-CSF was estimated to be 32,000.

The active fractions were collected and buffer exhange was performed against 40 mM sodium borate (pH 8.0) by the ultrafiltration apparatus mentioned above.

(3-2) TSKgel DEAE-5PW ion exchange high-performance liquid chromatography

The active eluate fraction obtained by the above procedure (3-1) was subjected to TSKgel DEAE-5PW ion exchange high-performance liquid chromatography under the following conditions.

Column: TSKgel DEAE-5PW (7.5 mm I.D.×75 mm, product of Tosoh Corporation)
Eluent A: 40 mM Sodium borate buffer (pH 8.0) containing 5% methanol
Eluent B: 40 mM Sodium borate buffer (pH 8.0) containing 1.0M NaCl and 5% methanol
Flow rate: 1.0 ml/min.
Fraction volume: 1.0 ml/tube/min.

| Concentration gradient: | Time (min) | B % |
| --- | --- | --- |
| | 0 | 0 |
| | 7 | 0 |
| | 42 | 30 |
| | 47 | 100 |
| | 52 | 100 |
| | 57 | 0 |
| | 62 | 0 |

Judging from the results (elution pattern) of the above TSKgel DEAE-5PW ion exchange high-performance liquid chromatography, the peaks observed with fractions Nos. 42–43 (NaCl concentration 0.23–0.25M) corresponded to M-CSF and said peaks were collected. Thus, purified M-CSF (*E.Coli*[3-153]M-CSF) was obtained from *Escherichia coli*.

Reference Example 3
Preparation of CHO[-32-522]M-CSF

A 930 ml quantity of a concentrated culture supernatant obtained by culturing CHO cells in the same manner as in Reference Example 1 was subjected to fractionation with ammonium sulfate. Fractions precipitated by 25–65% saturation with ammonium sulfate were obtained. Then the fractions were dissolved in distilled water (1180 ml) and purified by the following method. The detection of M-CSF was conducted, as in Reference Example 1, by Western blotting.

(1) ConA-Sepharose chromatography

A column (5×25 cm) packed with about 500 ml of ConA-Sepharose gel was equilibrated with 20 mM sodium phosphate buffer (pH 7.4) containing 0.15M NaCl, and the above solution was applied to the column. After thorough washing with the same buffer, elution was carried out with the same buffer containing 0.5M methyl α-D-mannoside. The whole eluate was concentrated by ultrafiltration using a YM-10 membrane, then buffer was exchanged to 20 mM sodium phosphate buffer (pH 7.4), and the resulting solution was subjected, in 5 aliquots, to anion exchange high-performance liquid chromatography.

(2) Anion exchange high-performance liquid chromatography

Column: TSKgel DEAE-5PW (21.5 mm ID×15 cm, product of Tosoh Corporation)
Eluent A: 40 mM Sodium phosphate buffer (pH 7.4)
Eluent B: 40 mM Sodium phosphate buffer (pH 7.4) containment 1.0M NaCl
Flow rate: 3.0 ml/min.

| Concentration gradient: | Time (min) | B % |
| --- | --- | --- |
| | 0 | 0 |
| | 10 | 0 |
| | 20 | 10 |
| | 95 | 30 |
| | 100 | 100 |
| | 110 | 100 |
| | 115 | 0 |
| | 130 | 0 |

AS a result of the above elution, the desired M-CSF was eluted into fractions Nos. 26–43. Main M-CSF fractions, i.e., fractions Nos. 30–39 were pooled, concentrated by ultrafiltration (using a YM-10 membrane) (15 ml) and purified, in 4 aliquots as follows.

(3) TSKgel Phenyl-5PWRP reversed-phase high-performance liquid chromatography

Column: TSKgel Phenyl-5PWRP (25.5 mm ID×15 cm, product of Tosoh Corporation)
Eluent A: 0.1% TFA
Eluent B: n-Propanol: 1.0% TFA (9:1)
Flow rate: 3 ml/min.
Fraction volume: 1.5 ml/tube/0.5 min.

| Concentration gradient: | Time (min) | B % |
| --- | --- | --- |
| | 0 | 0 |
| | 10 | 0 |
| | 20 | 20 |
| | 100 | 45 |
| | 120 | 100 |
| | 130 | 100 |
| | 140 | 0 |
| | 180 | 0 |

The M-CSF fractions of the above eluted fractions were pooled, concentrated by ultrafiltration (using a YM-10 membrane), further concentrated by Centricon 30 (product of Amicon) (1 ml), and subjected, in 3 aliquots, to gel filtration high performance liquid chromatography.

(4) Gel filtration high-performance liquid chromatography

Column: Superose 12HR 10/30 (10 mm ID×30 cm, product of Pharmacia LKB)

Eluent: 20 mM Sodium phosphate buffer (pH 7.4) containing 0.3M NaCl
Flow rate: 0.8 ml/min.
Fraction volume: 0.8 ml/tube/min.

As a result of the above chromatography, M-CSF was eluted in fractions Nos. 15–17, of which fraction No. 16 was pooled and subjected to experiment (5.6 mg, specific activity: $3.8 \times 10^7$ units/mg protein).

Reference Example 4

Improved isolation and purification of M-CSF derivative (*E. coli*[3-153]-M-CSF)

(1) Preparation of M-CSF fraction from *E. coli*

To 7.5 9 (Feet weight) of the *E. coli* strain SG21058 carrying plasmid ptrpIL-2X-M-CSF101 was added 1.0 ml of 50 nM Tris-hydrochloride buffer (pH 7.0), and the mixture was stirred thoroughly. Then, 6 ml of 4 mg/ml lysozyme and an amount of EDTA to make a final concentration of 10 mM were added, and the mixture was stirred at 4° C. for 15 minutes, then sonicated (20 KHz, 10 minutes, 200 W) and further centrifuged at 10,000×g/minute for 20 minutes to give a pellet. This was further washed With a buffer for washing (50 mM Tris-hydrochloride containing 2% Triton X100, pH 7.0) and again subjected to centrifugation under the same conditions. Two repetitions of this procedure gave an M-CSF fraction (pellet).

(2) Refolding of M-CSF from M-CSF fraction

To the M-CSF fraction obtained by the above procedure (1) was added 20 ml of 50 mM Tris-hydrochloride buffer (pH 7.0) containing 7M guanidine hydrochloride and 25 mM 2-mercaptoethanol, and the mixture was stirred at room temperature for at least 4 hours for dissolution. This solution was gradually added dropwise into a beaker already containing 2,000 ml of 50 mM Tris-hydrochloride buffer (pH 8.5) containing 0.5 mM reduced-form glutathione, 0.1 mM oxidized-form glutathione and 2M urea (with agitation with a stirrer). Then, the resultant mixture was alloyed to stand at 4° C. for at least 2 days. The solution was then centrifuged at 10,000×g/minute for 30 minutes. The precipitate was removed and the supernatant was recovered.

The refolded M-CSF occurs in the thus-obtained supernatant.

(3) Purification of M-CSF

The supernatant obtained by the above procedure (2) was purified in the following manner.

(3-1) Concentration by ion exchange chromatography

The refolded product solution obtained by the above procedure (2) was applied to a QAE-Zeta Prep 100 (product of Pharmacia-LBK) equilibrated in advance with 50 m Tris-hydrochloride buffer (pH 8.5) and, after thorough washing with the above-mentioned buffer, the M-CSF fraction was eluted with the above-mentioned buffer containing 0.5M NaCl.

(3-2) Hydrophobic high-performance liquid chromatography Ammonium sulfate was added to the fraction obtained in the above manner to give a 30%-saturated solution and the solution was centrifuged at 10,000×g/minutes for 20 minutes. The sediment was removed and the supernatant was recovered. This supernatant was passed through a 0.45-$\mu$m Millipore filter and then subjected to hydrophobic high-performance liquid chromatography under the following conditions.
Column: TSKgel Phenyl 5PW (21.5 mm I.D.×150 mm, product of Tosoh Corporation)
Eluent A: 30% Ammonium sulfate-saturated 40 mM sodium phosphate buffer (pH 7.4)
Eluent B: 40 mm Sodium phosphate buffer (pH 7.4)
Flow rate: 3.0 ml/min.
Fraction volume: 3.0 ml/tube/min.

| Concentration gradient: | Time (min) | B % |
| --- | --- | --- |
| | 0 | 0 |
| | 7 | 0 |
| | 47 | 100 |
| | 52 | 100 |
| | 57 | 0 |

As a result of the above, an M-CSF activity was eluted in fractions corresponding to the ammonium sulfate concentrations of 6–3%. Said active fractions were collected and subjected to buffer exchange to 40 mM sodium phosphate (pH 7.4) using an ultrafiltration apparatus.

(3—3) Anion exchange high-performance liquid chromatography

The fraction obtained by the above procedure (3-2 was subjected to anion exchange high-performance liquid chromatography under the following conditions.
Column: TSKgel DEAE-5PW (21.5 mm I.D.×150 mm, product of Tosoh Corporation)
Eluent A: 40 mM Sodium phosphate buffer (pH 7.4)
Eluent B: 40 mM Sodium phosphate buffer (pH 7.4) containing 1.0M NaCl
Flow rate: 3.0 ml/min.
Fraction volume: 3.0 ml/tube/min.

| Concentration gradient: | Time (min) | B % |
| --- | --- | --- |
| | 0 | 0 |
| | 5 | 0 |
| | 43 | 30 |
| | 48 | 100 |
| | 53 | 100 |
| | 58 | 0 |

From the result (elution pattern) of the above anion exchange high-performance liquid chromatography, the peaks observed with fractions Nos. 35 and 36 (NaCl concentration 0.28–0.29M) were found to correspond to the M-CSF. Said peaks were collected and thus the purified human M-CSF derivative (*E. coli*[3-153]-M-CSF) of the invention was obtained.

Reference Example 5

(1) Preparation of ptrpIL-2X-M-CSF201

The plasmid ptrpIL-2X-M-CSF101 was cleaved with the restriction enzymes BstEII and SalI and a 4.7 kb DNA fragment (I) containing the IL-2 and M-CSF DNA portions was obtained.

Separately, plasmid pcDM-CSF11 was cleaved with the restriction enzyme EcoRI. The cleavage ends were rendered blunt-ended using DNA polymerase I Klenow, fragment and then a SalI linker (5'-pGGTCGACC$_{OH}$3') (product of New England Biolabs) was ligated thereto. This ligation product was cleaved with the restriction enzymes SalI and BstEII to give a BstEII-SalI fragment (II) of about 1.1 kb.

The above-mentioned DNA fragments (I) and (II) were ligated together using T4 DNA ligase and the ligation product was used to transform competent cells of *E. coli* HB101 to give a desired transformant *E. coli* HB101 strain carrying the plasmid ptrpIL-2X-M-CSF201.

The thus-obtained plasmid ptrpIL-2X-M-CSF201 encodes two polypeptides within the transcription unit under the control of the *E. coli* tryptophan promoter. One is a 65-amino-acid polypeptide composed of methionine (translation initiation), amino terminal 60 amino acids of human IL-2 and 4 amino acids encoded by the synthetic DNA linker, and the other is a polypeptide comprising a human M-CSF derivative composed of Met (translation initiation) and those 520 amino acids covering the position-3 amino acid (Val) to the position-522 amino acid (Val) of the amino acid sequence defined by the formula (1).

In such two-cistron expression system, the translation of the second cistron is initiated by binding of a ribosome to the second SD sequence located in the synthetic DNA linker.

(2) Preparation of ptrpIL-2X-M-CSF202

The plasmid ptrpIL-2X-M-CSF201 was cleaved with the restriction enzymes NcoI and SalI and an NcoI-SalI DNA fragment of about 4.8 kb was recovered. Both ends of this DNA fragment was ligated to each other using synthetic oligodeoxynucleotides [5'-CATGGCCTGATAAG-3' and 5'-TCGACTTATCAGGC-3'] with T4 DNA ligase. Competent cells of E. coli HB101 were transformed with the ligation product and a desired transformant E. coli HB101 strain carrying the plasmid ptrpIL-2X-M-CSF202 as obtained.

The ptrpIL-2X-M-CSF202 obtained encodes a polypeptide comprising a human M-CSP derivative composed or met (translation initiation) and those 182 amino acids covering the position-3 amino acid (Val) to the position-84 amino acid (Ala) of the amino acid sequence defined by the Formula (1) in the second cistron within the transcription unit under the control of the E. coli tryptophan promoter.

(3) Preparation of ptrpIL-2X-M-CSF203

The plasmid ptrpIL-2X-M-CSF201 was cleaved with the restriction enzymes BamHI and SalI and a BamHI-SalI DNA fragment of about 4.9 kb was recovered. Both ends of this DNA fragment were ligated to each other using synethetic oligodeoxynucleotides [5'-GATCCATGATAAG-3' and 5'-TCGACTTATCATG-3' ] with T4 DNA<ligase and the ligation product was used to transform competent cells of E. coli HB101, whereby a desired E. coli HB101 transformant carrying the plasmid ptrpIL-2X-M-CSF203 was obtained.

The thus-obtained plasmid ptrpIL-2X-M-CSF203 encodes a polypeptide comprising a human M-CSF derivative composed of Met (translation initiation) and those 212 amino acids covering the position-3 amino acid (Val) to the position-214 amino acid (Pro) of the amino acid sequence defined by the formula (1) in the second cistron within the transcription unit under the control of the E. coli tryptophan promoter.

The above-mentioned E. coli HB101 strain carrying the plasmid ptrpIL-2X-M-CSF203 has been deposited, under the designation "Escherichia coli HB101/ptrpIL-2X-M-CSF203", with the Fermentation Research institute, Agency of Industrial Science and Technology under the deposition number FIRM P-11053 as of Oct. 18, 1989.

(4) Preparation of ptrpIL-2X-M-CSF204

The plasmid ptrpIL-2X-MS-CSF201 was cleaved with the restriction enzymes SmaI and SalI and a SmaI-SalI DNA fragment of about 5.0 kb was recovered. Both ends of this DNA fragment were ligated to each other using synthetic oligodeoxynucleotides [5'-GGGTGATAAG-3' and 5'-TCGACTTATCACCC-3'] with T4 DNA ligase and the ligation product was used to transform competent cells of E. coli HB101 to give a desired E. coli HB101 transformant carrying the plasmid ptrpIL-2X-M-CSF204.

The plasmid ptrpIL-2X-M-CSF204 thus obtained encodes a polypeptide comprising a human M-CSF derivative composed of Met (translation initiation) and those 256 amino acids covering the position-3 amino acid (Val) to the position-258 amino acid (Gly) of the amino acid sequence defined by the formula (1) in the second cistron within the transcription unit under the control of the E. coli tryptophan promoter.

(5) Preparation of ptrpIL-2X-M-CSF205

The plasmid ptrpIL-2X-M-CSF201 was cleaved with the restriction enzymes SphI and SalI and an SphI-SalI DNA fragment of about 5.1 kb was recovered. Both ends of this DNA fragment were ligated to each other using synthetic oligodeoxynucleotides [5'-CAGTGATAAG-3' and 5'-TCGACTTATCACTGCATG-3'] with T4 DNA ligase and the ligation product was used to transform competent cells of E. coli HB101 to give a desired E. coli HB101 transformant carrying the plasmid ptrpIL-2X-M-CSF205.

The thus obtained plasmid ptrpIL-2X-M-CSF205 encodes a polypeptide comprising a human M-CSF derivative composed of Met (translation initiation) and those 300 amino acids covering the position-3 amino acid (Val) to the position-302 amino-acid (Gln) of the amino acid sequence defined by the formula (1) in the second cistron Within the transcription unit under the control of the E. coli tryptophan promoter.

(6) Preparation of ptrpIL-2X-M-CSF206

The plasmid ptrpIL-2X-M-CSF201 was cleaved with the restriction enzymes KpnI and SalI and a KpnI-SalI DNA Fragment of about 5.2 kb was recovered. Both ends of this DNA fragment were ligated to each other using synthetic oligodeoxynucleotides [5'-CGCCTGATAAG-3' and 5'-TCGACTTATCAGGCGGTAC-3'] with T4 DNA ligase and the ligation product was used to transform competent cells of E. coli HB101 to give a desired E. coli HB101 transformant carrying the plasmid ptrpIL-2X-M-CSF206.

The thus-obtained plasmid ptrpIL-2X-M-CSF206 encodes a polypeptide comprising a human M-CSF derivative composed of Met (translation initiation) and those 332 amino acids covering the position-3 amino acid (Val) to the position-334 amino acid (Ala) of the amino acid sequence defined by the formula (1) in the second cistron within the transcription unit under the control of the E. coli tryptophan promoter.

(7) Expression of M-CSF derivatives

The plasmid respectively obtained by the above procedures (1) to (6) were each introduced into the E. coli strain SG2G21058 [J. Bacteriol., 164, 1124–1135 (1985)] by the transformation method and transformants [respectively designated E. coli SG21058/ptrpIL-2X-M-CSF201, E. coli SG21058/ptrpIL-2X-M-CSF202, E. coli SG21058/ptrpIL-2X-M-CSF203, E. coli SG21058/ptrpIL-2X-M-CSF204, E. coli SG21058/ptrpIL-2X-M-CSF205 and E. coli SG21053/ptrpIL-2X-M-CSF206] were obtained.

These transformants were cultivated in L3 medium (T. Maniatis, E. F. Fritsch and J. Sambrook, Molecular Cloning, A Laboratory Manual, p. 440 (1982), Cold Spring Harbor Laboratory) containing 50 g/ml ampicillin overnight at 37° C. A 0.5-ml portion of each culture was added to 50 ml of M9 medium (see the reference cited above) supplemented with 1% casamino acid, 5 µg/ml thiamine hydrochloride, 20 µg/ml L-cysteine and 50 µg/ml ampicillin with the glucose concentration adjusted to 0.4%, and shake culture was performed at 37° C. for 8 hours. Then cells were recovered by centrifugation (5,000 rpm), and the protein produced was analyzed by SDS-PAGE and Western blotting.

The Western blotting was performed using Bio-Rad's Transblot cells. Nitrocellulose membranes after transfer were blocked with PBS⁻ containing 1% bovine serum albumin, then reacted with a rabbit antiserum against M-CSF and further reacted with peroxidase-labeled goat anti-rabbit antibody (product of Bio-Rad Laboratories).

M-CSF band detection was performed by reacting the thus-obtained nltrocellulose membranes with a solution of the chromogenic substrate 4-chloro-1-naphthol.

In *E. coli* SC21058/ptrpIL-2X-M-CSF202, *E. coli* SG21058/ptrpIL-2X-M-CSF203, *E. coli* SG21058/ptrpIL-2X-M-CSF204, *E. coli* SG21058/ptrpIL-2X-M-CSF205 and *E. coli* SG21058/ptrpIL-2X-M-CSF206, the M-CSFs encoded in the second cistrons were respectively detected at positions corresponding to the expected molecular weights.

(8) Isolation and purification of M-CSF derivative (*E. coli* [3-2141-M-CSF)

To 10 g (wet weight) of *E. coli* SC21058 cells harboring the plasmid ptrpIL-2X-M-CSF203 obtained by the above procedure (3) was added 50 mM Tris-hydrochloride buffer (pH 7.0) to make the whole volume 100 ml, followed by thorough stirring. Then, 4 ml of 6 mg/ml lysozyme was added, 8 ml of 0.14M EDTA was further added, and the mixture was stirred at 4° C. for 15 minutes, then sonicated (200 KHz, 2 minutes, 200 W) and further centrifuged at 10,000 revolutions/minute for 20 minutes. The pellet obtained was thoroughly washed with 50 mM Tris-hydrochloride (pH 7.0) containing 2% Triton X-100 and again subjected to centrifugation under the same conditions to give an M-CSF fraction as the pellet.

To the thus-obtained M-CSF fraction was added 20 ml of 50 mM Tris-hydrochloride (pH 7.0) containing 7.0M guanidine hydrochloride and 50 mM mercaptoethanol, and the mixture was stirred at room temperature for 4 hours for reducing, denaturing and dissolving the protein. This solution was gradually added dropwise into a breaker already containing 2,000 ml of 50 mm Tris-hydrochloride (pH 8.5) containing 0.5 mM reduced-form glutathione, 0.1 mM oxidized-form, glutathione and 2M urea (with agitation with a stirrer) for 100-fold dilution. After completion of the dropping, the dilution was allowed to stand at 4° C. for at least 2 days and then centrifuged at 3,000 revolutions/minute for 30 minutes. The pellet was removed and the supernatant (2 liters) was recovered.

The refolded M-CSF exists in the thus-obtained supernatant.

One liter of the centrifugation supernatant obtained by the above procedure was concentrated using an ultrafiltration device (product of Amicon, with a YM-10 membrane (Amicon)), and the concentrate was centrifuged at 10,000 revolutions/minute for 20 minutes. The pellet was removed and the supernatant was recovered. To this supernatant was added ammonium sulfate in an amount sufficient for 30% saturation. The resultant mixture was again centrifuged in the same manner and the supernatant was subjected to hydrophobic interaction chromatography under the following conditions.

Column: TSKgel Phenyl 5PW (7.5 mm ID×75 mm, product of Tosoh Corporation)

Eluent A: 30% ammonium sulfate-saturated 50 mM sodium phosphate buffer (pH 7.4)

Eluent B: 50 mm Sodium phosphate buffer (pH 7.4)

Flow rate: 1.0 ml/min.

Fraction volume: 1 ml/tube/min.

| Concentration gradient: | Time (min) | B % |
|---|---|---|
| | 0 | 0 |
| | 7 | 0 |
| | 40 | 100 |
| | 45 | 100 |
| | 50 | 0 |
| | 60 | 0 |

As a result of the above procedure, an M-CSF activity was eluted in fractions Nos. 40–42 (ammonium sulfate concentration 8–6% saturation). The active fractions were collected, subjected to buffer exchange for 50 mM sodium phosphate (pH 7.4) using the above-mentioned ultrafiltration device, and then subjected to DEAE-5PW ion exchange high-performance liquid chromatography under the following conditions.

Column: DEAE-5PW (7.5 mm ID×75 mm, product of Tosoh Corporation)

Eluent A: 50 mM Sodium phosphate buffer (pH 7.4)

Eluent B: 50 mM Sodium phosphate buffer (pH 7.4) containing 1.0M NaCl

Flow rate: 1.0 ml/min.

Fraction volume: 1.0 ml/tube/min.

| Concentration gradient: | Time (min) | B % |
|---|---|---|
| | 0 | 0 |
| | 7 | 0 |
| | 42 | 30 |
| | 47 | 100 |
| | 52 | 100 |
| | 57 | 0 |

From the result (elution pattern) of the above DEAE-5PW ion exchange high-performance liquid chromatography, the peaks observed in fractions Nos. 31 and 32 (NaCl concentration 0.18–0.20M) corresponded to M-CSF. Said peaks were collected and a human M-CSF derivative of the present invention was obtained.

In the above purification steps, the activity of the human M-CSF derivative of the invention, the protein concentration, the specific activity and the degree of purification were determined. The results are shown below in Table 5.

TABLE 5

| Purification step | Volume (ml) | Activity (unit) | Protein (mg) | Specific activity (unit/mg protein) | Purification (fold) |
|---|---|---|---|---|---|
| Refolded solution | 1000 | $4.62 \times 10^7$ | 110 | $4.20 \times 10^5$ | 1.0 |
| 30% Ammonium Sulfate supernatant | 45 | $3.93 \times 10^7$ | 10.1 | $3.89 \times 10^6$ | 9.3 |
| Phenyl 5-PW HPLC | 3.6 | $1.50 \times 10^7$ | 1.82 | $8.24 \times 10^6$ | 19.6 |
| DEAE-5PW HPLC | 2.0 | $7.84 \times 10^6$ | 0.514 | $1.53 \times 10^7$ | 36.4 |

(9) SDS-PAGE of M-CSF derivative (*E. coli*[3-214]M-CSF)
Following the method of Laemmli [Laemmli, U.K., Nature, 277, 680 (1970)], the sample purified in the above manner was dissolved in each of Laemmli's sample buffers [2-ME⁺ and 2-ME⁻] and each solution was heat-treated at 95° C. for 5 minutes and then subjected to electrophoresis using a microslab gel (apparatus: product of Marisol Sangyo K.K. or Daiichi Chemical Co., Ltd.]. Prestained markers (product of Bio-Rad Laboratories) were used as molecular weight markers and Coomassie Brilliant Blue R-250 was used for staining.

As a result, the molecular weight of *E. coli*[3-214]M-CSF was found to be about 52,500 in the 2-ME⁻ state and about 26,900 in the 2-ME⁺ state and the electrophoresis gave a single band at each of said positions.

Reference Example 6

(1) Preparation of plasmid ptrpIL-2X-M-CSF109

The plasmid pcDM-CSF11-185 [prepared from the plasmid pcDM-CSFll containing an M-CSF gene (λcM11 cDNA, about 2.5 kb) (cf. Unexamined Japanese Patent Publication HEI 1-104176)] was digested smith the restriction enzymes ScaI and BamHI and a ScaI-BamHI DNA fragment (about 450 bp) was isolated and purified by agarose gel electrophoresis.

Then, a synthetic linker (B) shown below was ligated to the ScaI cleavage site of the thus obtained DNA fragment using T4 DNA ligase, whereby a XbaI-BamHI DNA fragment (about 480 bp) having an XbaI (restriction enzyme) cleavage site on the ScaI cleavage end side was obtained.

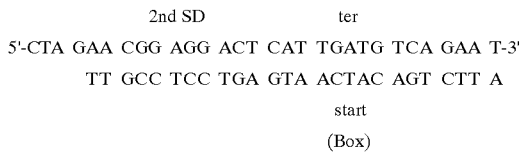

(Box)

The thus-obtained DNA fragment was inserted into the human IL-2 expression plasmid ptrpIL-2D8Δ (cf. Unexamined Japanese Patent Publication SHO 63-12958) between the XbaI and BamHI cleavage sites to give the desired plasmid, ptrpIL-2X-M-CSF109.

The plasmid ptrpIL-2X-M-CSF109 thus obtained encodes two polypeptides within the transcription unit under the control of the *E. coli* tryptophan promoter. One is a 65-amino-acid polypeptide composed of Met (translation initiation), amino terminal 60 amino acids of human IL-2 and 4 amino acids resulting from the synthetic linker DNA sequence, and the other is a polypeptide composed of Met (translation initiation) and 150 amino acids comprising the 4-position amino acid (Ser) to the 153-position amino acid (Thr) of the amino acid sequence defined by the formula (1).

(2) Preparation of ptrpIL-2X-M-CSF402

The plasmid ptrpIL-2X-M-CSF109 was cleaved with the restriction enzymes BstEII and ScaI and a DNA fragment of about 1.5 kb was recovered.

Separately, the plasmid ptrpIL-2X-M-CSF202 was cleaved in the same manner with the restriction enzymes BstEII and ScaI and a DNA fragment of about 3.3 kb was recovered.

Both the above DNA fragment was ligated to each other using T4 DNA ligase and the ligation mixture was used to transform competent cells of *E. coli* HB101 to give an *E. coli* HB101 transformant carrying the desired plasmid ptrpIL-2X-M-CSF402.

The thus-obtained plasmid ptrpIL-2X-M-CSF402 encodes, in the second cistron within the transcription unit under control of the *E. coli* tryptophan promoter, a polypeptide comprising Met (translation initiation) and a human M-CSF derivative composed of 181 amino acids from the 4-position amino acid (Ser) to the 184-position amino acid (Ala) of the amino acid sequence defined by the formula (1).

(3) Preparation of ptrpIL-2X-M.-CSF403

The plasmid ptrpIL-2X-M-CSF109 was cleaved with the restriction enzymes BstEII and ScaI and a DNA fragment of about 1.5 kb was recovered.

Separately, the plasmid ptrpIL-2X-M-CSF203 was cleaved in the same manner with the restriction enzymes BstEII and ScaI and a DNA fragment of about 3.4 kb was recovered.

Both the above DNA fragments were ligated to each other using T4 DNA ligase and the ligation mixture was used to transform competent cells of *E. coli* HB101, whereby an *E. coli* HB101 transformant carrying the desired plasmid ptrpIL-2X-M-CSF403 was obtained.

The thus-obtained plasmid ptrpIL-2X-M-CSF403 encodes, in the second cistron within the transcription unit under the control of the *E. coli* tryptophan promoter, a polypeptide comprising a human M-CSF derivative composed of Met (translation initiation) and 211 amino acids from the 4-position amino acid (Ser) to 214-position amino acid (Pro) of the amino acid sequence defined by the formula (1).

(4) Preparation of ptrpIL-2X-M-CSF404

The plasmid ptrpIL-2X-M-CSF109 was cleaved with the restriction enzymes BstEII and ScaI and a DNA fragment of about 1.5 kb Was recovered.

Separately, the plasmid ptrpIL-2X-M-CSF204 Was cleaved in the same manner with the restriction enzymes BstEII and ScaI and a DNA fragment of about 3.5 kb was recovered.

Both the above DNA fragments were ligated to each other using T4 DNA ligase and the ligation mixture was used to transform competent cells of *E. coli* HB101, whereby an *E. coli*. B101 transformant carrying the desired plasmid ptrpIL-2X-M-CSF404 was obtained.

The thus-obtained plasmid ptrpIL-2X-M-CSF404 encodes, in the second cistron within the transcription unit under the control of the *E. coli* tryptophan promoter, a polypeptide comprising a human M-CSF derivative composed of Met (translation initiation) and 255 amino acids from the 4-position amino-acid (Ser) to the 258-position amino acid (Gly) of the amino acid sequence defined by the formula (1).

(5) Preparation of ptrpIL-2X-M-CSF405

The plasmid ptrpIL-2X-M-CSF109 was cleaved with the restriction enzymes BstEII and ScaI and a DNA fragment of about 1.5 kb was recovered.

Separately, the plasmid ptrpIL-2X-M-CSF205 was cleaved in the same manner with the restriction enzymes BstEII and ScaI and a DNA fragment of about 3.6 kb was recovered.

Both the above DNA fragments were ligated to each other using T4 DNA ligase and the ligation mixture was used to transform competent cells of *E. coli* HB101, whereby an *E. coli* HB101 transformant carrying the desired plasmid ptrpIL-2X-M-CSF405 was obtained.

The thus-obtained plasmid ptrpIL-2X-M-CSF405 encodes, in the second cistron within the transcription unit under the control of the *E. coli* tryptophan promoter, a polypeptide comprising a human M-CSF derivative composed of Met (translation initiation) and 299 amino acids from the 4-position amino acid (Ser) to the 302-position amino acid (Gln) of the amino acid sequence defined by the formula (1).

(6) Preparation of ptrpIL-2X-M-CSF406

The plasmid-ptrpIL-2X-M-CSF109 was cleaved with the restriction enzymes BstEII and ScaI and a DNA fragment of about 1.5 kb was recovered.

Separately, the plasmid ptrpIL-2X-M-CSF206 was cleaved in the same manner with the restriction enzymes BstEII and ScaI and a DNA fragment of about 3.7 kb was recovered.

Both the above DNA fragments were ligated to each other using T4 DNA ligase and the ligation mixture was used to transform competent cells of *E. coli* HB101, whereby an *E. coli* HB101 transformant carrying the desired plasmid ptrpIL-2X-M-CSF406 was obtained.

The thus-obtained plasmid ptrpIL-2X-M-CSF406 encodes, in the second cistron within the transcription unit under the control of the *E. coli* tryptophan promoter, a polypeptide comprising a human M-CSF derivative composed of Met (translation initiation) and 331 amino acids from the 4-position amino acid (Ser) to the 334-position amino acid (Ala) of the amino acid sequence defined by the formula (1).

(7) Expression of M-CSF derivatives

The plasmids respectively obtained by the above procedures (1) to (6) were each introduced into the *E. coli* strain SG21058 [J. Bacteriol., 164, 1124–1135 (1985)] by the transformation method to give transformants [respectively designated *E. coli* SG21058/ptrpIL-2X-M-CSF109, *E. coli* SG21058/ptrpIL-2X-M-CSF402, *E. coli* SG21058/ptrpIL-2X-M-CSF403, *E. coli* SC21058/ptrpIL-2X-M-CSF404, *E. coli* SG21058/ptrpIL-2X-M-CSF405 and *E. coli* SG21058/ptrpIL-2X-M-CSF406].

These transformants were cultured in LB medium (T. Maniatis, E. F. Fritsch and J. Sambrook, Molecular Cloning, A Laboratory Manual, p. 440 (1982), Cold Spring Harbor Laboratory) containing 50 µg/ml ampicillin overnight at 37° C. A 0.5-ml portion of each culture was added to 50 ml of M9 medium (cf. the reference cited above) with 1% casamino acid, 5 µg/ml thiamine hydrochloride, 20 µg/ml L-cysteine and 50 µg/ml ampicillin added and the glucose concentration adjusted to 0.4% and, after 8 hours of shake culture at 37° C., cells were recovered by centrifugation (5,000 rpm), and the protein produced was analyzed, in the same manner as in Reference Example 5-(7), by SDS-PAGE and Western blotting.

As a result, the M-CSFs each encoded in the second cistron were detected in positions corresponding to the respective expected molecular weights for *E. coli* SG21058/ptrpIL-2X-M-CSF109, *E. coli* SG21058/ptrpIL-2X-M-CSF402, *E. coli* SG21058/ptrpIL-2X-M-CSF403, *E. coli* SG21058/ptrpIL-2X-M-CSF404, *E. coli* SG21058/ptrpIL-2X-M-CSF405 and *E. coli* SG21058/ptrpIL-2X-M-CSF406.

(8) Isolation and purification of M-CSF derivative (*E. coli* [4-153]-M-CSF)

[1] Preparation of M-CSF fraction from *E. coli*

To 7.5 g (wet weight) of *E. coli* SG21058 strain carrying the plasmid ptrpIL-2X-M-CSF109 obtained by the above procedure (1) was added 50 mM Tris-hydrochloride buffer (pH 7.0) to make the whole volume 100 ml, followed by thorough stirring. Then, 6 ml of 2 mg/ml lysozyme was added, and then 4 ml of 0.14M EDTA was added. The mixture was stirred at 4° C. for 15 minutes, and then sonicated (20 KHz, 10 minutes, 200 W) and further centrifuged at 10,000 revolutions/minute for 20 minutes to give a pellet. This was further washed with a buffer for washing (50 mM Tris-hydrochloride buffer containing 2% Triton X-100, pH 7.0) and again centrifuged under the same conditions. After repeating this procedure twice, an M-CSF fraction (pellet) was obtained.

[2] Refolding of M-CSF from M-CSF fraction

To the M-CSF fraction obtained by [1] above was added 20 ml of 50 mM Tris-hydrochloride buffer (pH 7.0) containing 7M guanidine hydrochloride and 25 mM 2-mercaptoethanol, and the mixture was stirred at room temperature for at least 4 hours for reducing, denaturing and dissolving the protein. This solution was gradually added dropwise into a breaker already containing 2,000 ml of 50 nM Tris-hydrochloride (pH 8.5) containing 0.5 mM reduced-form glutathione, 0.1 mM oxidized-form glutatione and 2M urea (with agitation with a stirrer) and the resultant mixture was allowed to stand at 4° C. for at least 2 days. The solution was then centrifuged at 3,500 revolutions/minute for 30 minutes, and the pellet was removed and the supernatant was recovered.

The refolded M-CSF was present in the thus-obtained supernatant.

[3] Purification of M-CSF

The centrifugation supernatant obtained by [2] above was purifed in the following manner.

[3-1] Hydrophobic high-performance liquid chromatography

The above centrifugation supernatant was concentrated by an ultrafiltration device (product of Amicon, with a YM-10 membrane (Amicon) used), and ammonium sulfate was added to the concentrate to make a 30%-saturated solution. The resultant solution was centrifuged at 10,000 revolutions/minute for 20 minutes. The pellet was removed and the supernatant was recovered. This supernatant was passed through a 0.45-µm Millipore filter and then subjected, in two portions, to hydrophobic interaction chromatography under the following conditions.

Column: TSKgel Phenyl 5PW (7.5 mm ID×75 mm, product of Tosoh Corporation)
Eluent A: 30% Ammonium sulfate-saturated 40 mM sodium phosphate buffer (pH 7.4)
Eluent B: 40 mM Sodium phosphate buffer (pH 7.4)
Flow rate: 1.0 ml/min.
Fraction volume: 1 ml/tube/min.

| Concentration gradient: | Time (min.) | B % |
| --- | --- | --- |
| | 0 | 0 |
| | 7 | 0 |
| | 40 | 100 |
| | 45 | 100 |
| | 50 | 0 |

As a result, an M-CSF activity was eluted in fractions corresponding to the ammonium sulfate concentration of 11–6%. Said active fractions were collected, and subjected to buffer exchange for 40 mm sodium phosphate (pH 7.4) using the above-mentioned ultrafiltration device.

[3-2] Anion exchange high-performance liquid chromatography

The fraction obtained by the above procedure [3-1] was subjected, in 4 portions, to DEAE-5PW anion exchange high-performance liquid chromatography under the following conditions.

Column: TSKgel DEAE-5PW (7.5 mm ID×75 mm, product of Tosoh Corporation)
Eluent A: 50 mM Sodium phosphate buffer (pH 7.4)
Eluent B: 50 mM Sodium phosphate buffer (pH 7.4) containing 1.0M NaCl Flow rate: 1.0 ml/min.
Fraction volume: 1.0 ml/tube/min.

| Concentration gradient: | Time (min.) | B % |
|---|---|---|
| | 0 | 0 |
| | 5 | 0 |
| | 55 | 30 |
| | 60 | 100 |
| | 65 | 100 |
| | 70 | 0 |

From the result (elution pattern) of the above DEAE-5PW ion exchange high-performance liquid chromatography, the peaks observed in fractions Nos. 41 and 42 (NaCl concentration 0.21–0.22M) were found to correspond to M-CSF. Said peaks were collected to give the purified human M-CSF derivative (E. coli[4-153]-M-CSF) of the invention.

(9) Determination of N-terminal amino acid sequence of M-CSF derivative (E. coli[4-153]-M-CSF)

The N-terminal amino acid sequence of the M-CSF derivative (E. coli[4-153]-M-CSF) obtained by the above procedure (8)-[3-2] was determined using a gaseous phase sequencer (product of Applied Biosystems).

As a result, the sequence Ser-Glu-Tyr-X'-Ser and the sequence Met-Ser-Glu-Tyr-X'-Ser were found in a ratio of about 7–8 to 1.

In the sequences mentioned above, the amino acid X' could not be identified but was estimated to be Cys based on the gene structure.

Bioavailability

Bioavailability serves as an index of whether or not the drug administered is effectively utilized in the living body.

Herein, the bioavailability is expressed by the ratio of blood half-life in the case of intravenous injection and blood half-life in the case of subcutaneous injection in terms of integration value.

The blood half-life was determined by RIA. The integration value of the blood half-life was determined by the trapezoidal rule, and bioavailability was calculated according to the following equation.

Bioavailability (%)=$AUC_{sc}/AUC_{iv} \times 100$ (1) Blood half-life measurement The M-CSF derivative (E. coli[3-153]-M-CSF) and CHO [-32-522]-M-CSF obtained in Reference Example 1 were each diluted with MSA (mouse serum albumin)-containing physiological saline (30 μg/ml) to a concentration of 20 μg/ml and these were administered to groups of 4 mice (BALB/c males, 7 weeks of age) intravenously (i.v.) at a dose of 0.25 ml per mouse (200 μg/kg). After administration, the amount of M-CSF in blood was determined by RIA at timed intervals.

The blood half-life measurment by said RIA was carried out by the following method. Thus, a mixture of 100 μl of the test sample (serum) or a standard M-CSF (M-CSF derivative (E. coli[3-153]-M-CSF) obtained in Reference Example 2) solution, 100 1 of a solution containing 10,000 cpm (per 100 μl) of Na$^{125}$I-labeled M-CSF (derived from the above-mentioned standard M-CSF by labeling with $^{125}$I by the iodogen method) and 200 μl of an anti-M-CSF rabbit antiserum (prepared by 40,000-fold dilution of the polyclonal antibody OCT511 obtained by the method to be mentioned later herein with 0.1% BSA/PBS/0.05% thimerosal) is allowed to stand at room temperature for 20 hours or at 4° C. for 48 hours to thereby allow the antigen-antibody reaction to occur. After completion of the reaction, the labeled M-CSF-bound product and the non-bound product are separated by the two-antibody method. For this separation, 100 μl of a normal rabbit serum 400-fold diluted with 0.1% BSA/PBS/0.05% thimerosal, 100 μl of an anti-rabbit IgG serum 40-fold diluted in the same manner and 200 μl of 12.5% polyethylene glycol solution in PBS are first added, the reaction is allowed to proceed at 4° C. for 30 minutes, and centrifugation is performed at 3,000 rpm for 15 minutes, followed by decantation to give a labeled M-CSF-antibody conjugate as the precipitate. The precipitate is counted with a gamma counter for 1 minute. A standard curve is prepared using standard solutions, and the number of counts measured similarly by repeating the above procedure with respect to the test sample containing the M-CSF derivative of the invention is plotted on the standard curve, and the M-CSF concentration in said test sample is determined.

The results thus obtained are shown below in Table 6.

TABLE 6

| Time (min) | CHO [-32-522]- M-CSF | E. coli [3-153]- M-CSF | E. coli[3-214]- M-CSF |
|---|---|---|---|
| M-CSF (I.V. Administration) | | | |
| 5 | 1335 | 2078 | 3850 |
| 15 | 891 | 304 | 3368 |
| 30 | 623 | 41 | 2715 |
| 60 | 434 | 12 | 1751 |
| 120 | 272 | 4 | 447 |
| 240 | 44 | — | 124 |
| 360 | 10 | — | 19 |
| Half-life | 53.0 min | 14.4 min. | 46.2 min |
| M-CSF (S.C. Administration) | | | |
| 15 | — | 17.21 | — |
| 30 | 1.52 | 58.85 | 6.55 |
| 60 | 1.65 | 78.63 | 24.27 |
| 120 | 4.61 | 98.12 | 108.91 |
| 240 | 9.81 | 56.88 | 138.33 |
| 480 | 11.32 | 4.70 | 62.33 |
| 720 | 7.16 | — | — |
| Half-life | 362.9 min | 79.5 min | 208.7 min |

In the table, the unit is ng/ml.

Bioavailabilities of CHO[-32-522]-M-CSF and E. coli[3-153]-M-CSF were calculated from the results of Table 6 above with the results shown below,

CHO[-32-522]-M-CSF:

(5876.6/85087.5)×100=6.63%

E. coli[3-1531]-M-CSF:

(24519.9/20966.5)×100=116.95%

E. coli[3-214]-M-CSF:

(44602.0/267107.0)×100=16.70%

As clear from the above, the M-CSF derivative E. coli [3-153]-M-CSF of the invention has a good delivery into blood by subcutaneous administration, and is suggested to have superior bioavailability by subcutaneous administration to that of CHO[-32-522]-M-CSF, and therefore it is believed to be particularly suitable as an anti-allergic agent which is usually administered subcutaneously.

The polyclonal antibody against M-CSF as used in the above RIA has the following properties.

1) The polyclonal antibody used in the above procedure was prepared by the following method.

For polyclonal antibody production, female New Zealand white rabbits weighing 2.5 kg to 3.0 kg were subjected to multipoint intracutaneous immunization with 20 μg/animal of a purified sample of CHO[-32-522]-M-CSF (dissolved in PBS) together with the equal amount of Freund's complete adjuvant, followed by immunizations with 20 μg of the same sample together with Freund's imcomplete adjuvant at one-month intervals. The number of immunizations, inclusive of the first one, amounted to 7. One week after completion of the immunization procedure, the whole blood was collected from the rabbits and antisera were obtained.

One of the three antibodies obtained was designated as OCT511 and stored at −80° C.

2) The polyclonal antibody OCT511 to be used in the determination of blood half-life of each of the M-CSF derivatives has the following properties.

[1] Antibody titer

CHO[-32-522]-M-CSF was labeled with $^{125}$I by the Iodogen method and the antibody titer was defined as the dilution factor for the antiserum capable of binding 50% of 10 kcpm of this $^{125}$I-labeled CHO[-32-522]-M-CSF.

As a result, the antibody titer of OCT511 was 80,000.

[2] Neutralizing activity

The neutralizing activity was determined by the colony assay method using mouse bone marrow cells. The neutralizing activity of OCT511 was such that 1 ml of OCT511 could neutralize 1 to $2 \times 10^6$ units of CHO[-32-522]-M-CSF.

[3] Cross-reactivity

This OCT511 did not cross-react with mouse CSF (L-cell culture supernatant) or with human GM-CSF (Amersham) at all. Furthermore, it did not cross-react at all with human IL-1α (cf. Unexamined Japanese Patent Publication SHO 63-164899), IL-1β (cf. Unexamined Japanese Patent Publication SHO 63-152398), IL-2 (Amersham) or TNF-α (Amersham).

EXAMPLE 5

The effect of E. coli[3-153]M-CSF on picryl chloride-induced delayed type hypersensitive skin reaction (PC-DTH) in mouse which is widely used as an assay for cellular immunity was investigated.

The following materials were used.

Mice: 8-week-old male BALB/c mice (SL C), 5 mice in each group, were used.

Antigen solution: As an antigen for sensitization, a solution prepared by dissolving picryl chloride (PC) (product of Nakarai Kagaku Yakuhin) in ethanol to a concentration of 0.5% (w/v) was used. As an antigen for challenge, a solution of picryl chloride dissolved in olive oil to a concentration of 1% (w/v) was used.

Apparatus for measurement:

Dial thickness gauge (product of Ozaki Seisakusho) was used

Method of sensitization:

Sensitization was conducted by application to the ears of mice. The application was carried out according to the method of Tajima et al (Shigeru TAJIMA, Eiko IMAI, Keizo ITO and Takashi NOSE: "Simplified method in sensitization to picryl chloride for induction of delayed type hypersensitivity in mice", Igaku no Ayumi, Vol. 122, No. 4, pp 240–242, 1982).

That is to say, the antigen for sensitization was applied to the front and rear sides of the right ear each in an amount of 10 μl with micropipet. Four days after the sensitization, the thickness of the left ear was measured. This was used as the pre-reaction value. Thereafter, the above antigen solution for challenge was applied to the front and rear sides of the left ear each in an amount of 5 μl, and 24 hours thereafter the thickness of the left ear was measured, and the difference (ΔT) between this thickness and the pre-reaction value was designated increase in the ear thickness.

The percent inhibition relative to the control group can be determined by the following equation.

Percent inhibition (%)

After Control=1-(ΔT of M-CSF-treated group/ΔT of control)×100

E. coli[3-153]M-CSF was administered in the following manner.

E. coli[3-153]M-CSF was adjusted to a concentration of 10 or 100μg/kg per mouse with physiological saline containing mouse serum albumin (MSA) and administered subcutaneously. The treated groups were as follows.

The group that received the solvent (physiological saline containing 30 μg/ml MSA) was used as control group. Said group was treated in the same manner as the following treated group No. 1.

Treated Groups

No. 1: a group in which the drug was given after sensitization and thereafter administered for 3 consecutive days with challenge conducted on the fourth day.

No. 2: a group in which the drug was given after sensitization and thereafter administered for 3 consecutive days with challenge conducted on the fourth day, followed by a single administration.

No. 3: a group in which the drug was administered for 3 consecutive days before sensitization and again administered after the sensitization and for 3 consecutive days thereafter with challenge conducted on the fourth day.

No. 4: a group in which the drug was administered for 3 consecutive days before sensitization and again administered after the sensitization and for 3 consecutive days thereafter with challenge conducted on the fourth day, followed by a single administration.

The results are shown in Table 7 below.

TABLE 7

|  | Increase in ear thickness |
| --- | --- |
| Administration of M-CSF (10 μg/kg) | |
| Treated Group 1 | 12.1 ± 0.6 |
| Treated Group 2 | 12.1 ± 1.8 |
| Treated Group 3 | 12.9 ± 0.5 |
| Treated Group 4 | 9.1 ± 1.4 |
| Administration of M-CSF (100 μg/kg) | |
| Treated group 1 | 8.8 ± 1.7 |
| Treated group 2 | 13.4 ± 2.3 |
| Treated group 3 | 14.2 ± 0.3 |
| Treated group 4 | 10.1 ± 1.1 |
| Control group | 20.1 ± 1.5 |

The increase in ear thickness is expressed in terms of mean±SE and the unit thereof is $\times 10^2$/mm.

As a result of this example, induction of DTH was inhibited in any of the treated groups to a larger extent compared with the control group.

In treated groups 1 wherein M-CSF was administered at a dose of 10 or 100 μg/kg, inhibitions of comparable degree were observed. In treated groups 2 and 3, stronger inhibition was observed at 10 μ/kg rather than at 100 μg/kg. In treated groups 4, about 50% inhibition was observed at 10 and 100 μg/kg.

The above results suggests that the induction of DTH with M-CSF is strongly inhibited in the group in which M-CSF was administered before sensitization and, after sensitization, consecutively administered, followed by challenge and subsequent single administration.

EXAMPLE 6

The administration timing of E. coli[3-153]M-CSF was checked with respect to its effect on mouse PC-DTH using a method of Example 5.

E. coli[3-153]M-CSF was diluted with physiological saline containing MSA (30 μg MSA/ml) and administered at doses of 1, 10 and 100 μg/kg with the administration timing as shown below via subcutaneous route (sc) while a group that received a solvent (physiological saline containing MSA) served as a control group.

Treated Group

I: a group wherein the drug was administered after sensitization with challenge conducted on the fourth day.
II: a group wherein the drug was administered after sensitization and thereafter administered for 2 consenecutive days with challenge conducted on the fourth day.
III: a group wherein the drug was administered after sensitization and thereafter administered for 3 consecutive days with challenge and drug administration conducted on the fourth day.
IV: a group which is treated in the same manner as in treated group III except that the drug was administered twice a day.
V: a group wherein the drug was not administered before challenge, but administered three times at the time of challenge, i.e., 4 hours before challenge, concurrently with challenge and 4 hours after challenge.

Table 8 shows the results.

TABLE 8

| | | E. coli[3-153] M-CSF (S. C. administration) | | |
|---|---|---|---|---|
| Group | solvent | 1 μg/kg | 10 μg/kg | 100 μg/kg |
| I | 21.6 ± 2.9 | 24.2 ± 1.9 | 18.5 ± 4.8 (14.4%) | 18.4 ± 3.7 (14.8%) |
| II | 26.6 ± 2.2 | 25.0 ± 3.0 (6.0%) | 18.6 ± 2.2* (30.1%) | 13.8 ± 1.9** (48.1%) |
| III | 24.0 ± 1.1 | 15.3 ± 1.3** (36.3%) | 15.5 ± 2.0 (35.4%) | 13.1 ± 2.6* (45.4%) |
| IV | 23.8 ± 1.0 | 21.3 ± 1.3 (10.5%) | 16.5 ± 1.5** (30.7%) | 13.4 ± 2.8* (43.7%) |
| V | 26.7 ± 1.3 | 24.2 ± 2.0 (9.4%) | 23.6 ± 3.5 (11.6%) | 18.7 ± 2.5* (30.0%) |

The values indicate increase in ear thickness (Mean ± SE), and the unit is × $10^2$ mm$^2$
The values in parentheses show percent inhibition.
*: $p < 0.05$
**: $p < 0.01$ As a result, significant inhibitory effect was observed at a dose of 10 μg/kg or more in groups II to IV wherein the drug was administered 3 times or 5 times or administered 5 times, each twice a day during the 4 days period from the primary sensitization to the secondary sensitization. Furthermore, significant inhibitory effect was also observed in group V wherein the drug was administered after the establishment of DTH.

EXAMPLE 7

Three kinds of M-CSFs, i.e., E. coli[3-153]M-CSF, E. coli[3-214]M-CSF and CHO[-32-522] were tested for ability to inhibit mouse PC-DTH.

Each of the M-CSFs was diluted with plysiological saline containing MSA (30 μg/ml) and administered at doses of 1, 10 and 100 μg/kg subcutaneously (SC) and interavenously (IV).

The administration timing was the same as treated group III in Example 6. Namely, the drug was administered after sensitization and for 3 consecutive days thereafter, followed by challenge and administration on the fourth day. Other procedures are the same as in Examples 5 and 6.

The results are shown in Table 9 and Table 10.

In the case of intravenous administration, CHO(-32-522) M-CSF and E. coli[3-214]M-CSF exhibited dose-dependent inhibition tendency and achieved clear inhibition at 100 μg/kg. While E. coli[3-153]M-CSF exhibited inhibition at lower doses (1 μ/g, 10 μg/kg), the degree of inhibition was weak.

In the case of subcutaneous administration, the 3 kinds of M-CSFs exhibited inhibition tendency, and strong ihibition was observed only for E. coli[3-153]M-CSF. It became clear from the foregoing that the DTH inhibition reaction is common to the M-CSFs and that E. coli[3-153]M-CSF is excellent in the case of subcutaneous administration. This result is in agreement with the results of bioavailability obtained by subcutaneous administration (Table 6). It is strongly suggested that E. coli[3-153]M-CSF is a derivative having excellent properties particularly as M-CSF for subcutaneous injection.

TABLE 9

| | Intravenous Administration | | |
|---|---|---|---|
| | 1 μg/kg | 10 μg/kg | 100 μg/kg |
| CHO(-32-522) | | | |
| M-CSF (Lot 9J-72) E. coli(3-214) | 28.4 ± 1.4 | 25.3 ± 1.2 (10.0%) | 21.8 ± 1.8* (22.4%) |
| M-CSF (Lot 9I-98) E. coli(3-153) | 26.3 ± 1.5 (6.4%) | 24.3 ± 1.0 (13.5%) | 18.7 ± 1.8** (33.5%) |
| M-CSF (Lot 9J-81) | 24.2 ± 0.6* (13.9%) | 21.0 ± 1.7* (25.3%) | 23.7 ± 2.6 (15.7%) |
| Solvent | | 28.1 ± 1.5 | |

TABLE 10

| | Subcutaneous Administration | | |
|---|---|---|---|
| | 1 μg/kg | 10 μg/kg | 100 μg/kg |
| CHO(-32-522) | | | |
| M-CSF (Lot 9J-72) E. coli(3-214) | 27.2 ± 0.7 (0%) | 22.5 ± 4.1 (17.3%) | 24.8 ± 1.9* (8.8%) |
| M-CSF (Lot 9I-98) E. coli(3-153) | 22.7 ± 1.7 (16.5%) | 23.1 ± 1.5 (15.1%) | 22.5 ± 1.4 (17.3%) |
| M-CSF (Lot 9J-81) | 22.6 ± 2.5* (16.9%) | 23.5 ± 1.5* (13.6%) | 17.3 ± 2.1* (36.4%) |
| Solvent | | 27.2 ± 1.8 | |

The values indicate increase in ear thickness (Mean ±SE). The unit is ×$10^{-2}$ mm$^2$. The values in parentheses shore percent inhibition.
* $p<0.05$,
** $p<0.01$ Other embodiments of the invention will be apparent to those skilled in the art from a consideration of the specification and practice of the invention disclosed herein. It is intended that the specification and examples be considered as exemplary only, with a true scope and spirit of the invention being indicated by the claims.

SEQUENCE LISTING ( 1 ) GENERAL INFORMATION:

( i i i ) NUMBER OF SEQUENCES: 1

( 2 ) INFORMATION FOR SEQ ID NO:1:

( i ) SEQUENCE CHARACTERISTICS:
        ( A ) LENGTH: 554 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:1:

```
Met Thr Ala Pro Gly Ala Ala Gly Arg Cys Pro Pro Thr Thr Trp Leu
  1               5                  10                  15
Gly Ser Leu Leu Leu Leu Val Cys Leu Leu Ala Ser Arg Ser Ile Thr
             20                  25                  30
Glu Glu Val Ser Glu Tyr Cys Ser His Met Ile Gly Ser Gly His Leu
         35                  40                  45
Gln Ser Leu Gln Arg Leu Ile Asp Ser Gln Met Glu Thr Ser Cys Gln
     50                  55                  60
Ile Thr Phe Glu Phe Val Asp Gln Glu Gln Leu Lys Asp Pro Val Cys
 65                  70                  75                  80
Tyr Leu Lys Lys Ala Phe Leu Leu Val Gln Xaa Ile Met Glu Asp Thr
                 85                  90                  95
Met Arg Phe Arg Asp Asn Thr Pro Asn Ala Ile Ala Ile Val Gln Leu
                100                 105                 110
Gln Glu Leu Ser Leu Arg Leu Lys Ser Cys Phe Thr Lys Asp Tyr Glu
            115                 120                 125
Glu His Asp Lys Ala Cys Val Arg Thr Phe Tyr Glu Thr Pro Leu Gln
        130                 135                 140
Leu Leu Glu Lys Val Lys Asn Val Phe Asn Glu Thr Lys Asn Leu Leu
145                 150                 155                 160
Asp Lys Asp Trp Asn Ile Phe Ser Lys Asn Cys Asn Asn Ser Phe Ala
                165                 170                 175
Glu Cys Ser Ser Gln Asp Val Val Thr Lys Pro Asp Cys Asn Cys Leu
                180                 185                 190
Tyr Pro Lys Ala Ile Pro Ser Ser Asp Pro Ala Ser Val Ser Pro His
            195                 200                 205
Gln Pro Leu Ala Pro Ser Met Ala Pro Val Ala Gly Leu Thr Trp Glu
    210                 215                 220
Asp Ser Glu Gly Thr Glu Gly Ser Ser Leu Leu Pro Gly Glu Gln Pro
225                 230                 235                 240
Leu His Thr Val Asp Pro Gly Ser Ala Lys Gln Arg Pro Pro Arg Ser
                245                 250                 255
Thr Cys Gln Ser Phe Glu Pro Pro Glu Thr Pro Val Val Lys Asp Ser
                260                 265                 270
Thr Ile Gly Gly Ser Pro Gln Pro Arg Pro Ser Val Gly Ala Phe Asn
            275                 280                 285
Pro Gly Met Glu Asp Ile Leu Asp Ser Ala Met Gly Thr Asn Trp Val
```

```
                290                         295                         300
    Pro  Glu  Glu  Ala  Ser  Gly  Glu  Ala  Ser  Glu  Ile  Pro  Val  Pro  Gln  Gly
    305                      310                      315                     320

Thr  Glu  Leu  Ser  Pro  Ser  Arg  Pro  Gly  Gly  Gly  Ser  Met  Gln  Thr  Glu
                        325                      330                     335

Pro  Ala  Arg  Pro  Ser  Asn  Phe  Leu  Ser  Ala  Ser  Ser  Pro  Leu  Pro  Ala
                   340                      345                     350

Ser  Ala  Lys  Gly  Gln  Gln  Pro  Ala  Asp  Val  Thr  Gly  Thr  Ala  Leu  Pro
              355                      360                     365

Arg  Val  Gly  Pro  Val  Arg  Pro  Thr  Gly  Gln  Asp  Trp  Asn  His  Thr  Pro
         370                      375                     380

Gln  Lys  Thr  Asp  His  Pro  Ser  Ala  Leu  Leu  Arg  Asp  Pro  Pro  Glu  Pro
    385                      390                          395                    400

Gly  Ser  Pro  Arg  Ile  Ser  Ser  Pro  Arg  Pro  Gln  Gly  Leu  Ser  Asn  Pro
                        405                      410                     415

Ser  Thr  Leu  Ser  Ala  Gln  Pro  Gln  Leu  Ser  Arg  Ser  His  Ser  Ser  Gly
                   420                      425                     430

Ser  Val  Leu  Pro  Leu  Gly  Glu  Leu  Glu  Gly  Arg  Arg  Ser  Thr  Arg  Asp
              435                      440                     445

Arg  Arg  Ser  Pro  Ala  Glu  Pro  Glu  Gly  Gly  Pro  Ala  Ser  Glu  Gly  Ala
         450                      455                     460

Ala  Arg  Pro  Leu  Pro  Arg  Phe  Asn  Ser  Val  Pro  Leu  Thr  Asp  Thr  Gly
    465                      470                          475                    480

His  Glu  Arg  Gln  Ser  Glu  Gly  Ser  Ser  Ser  Pro  Gln  Leu  Gln  Glu  Ser
                        485                      490                     495

Val  Phe  His  Leu  Leu  Val  Pro  Ser  Val  Ile  Leu  Val  Leu  Leu  Ala  Val
                   500                      505                     510

Gly  Gly  Leu  Leu  Phe  Tyr  Arg  Trp  Arg  Arg  Arg  Ser  His  Gln  Glu  Pro
              515                      520                     525

Gln  Arg  Ala  Asp  Ser  Pro  Leu  Glu  Gln  Pro  Glu  Gly  Ser  Pro  Leu  Thr
         530                      535                     540

Gln  Asp  Asp  Arg  Gln  Val  Glu  Leu  Pro  Val
    545                      550
```

We claim:

1. A method of treating a Type I allergy or a Type IV allergy comprising administering biologically active macrophage-colony stimulating factor (M-CSF), wherein said macrophage-colony stimulating factor is a macrophage-colony stimulating factor having an amino acid primary sequence of Val at position 3 or Ser at position 4 to Thr at position 153 or an amino acid primary sequence of Val at position 3 or Ser at position 4 to Pro at position 214, or an amino acid primary sequence of Met at position -32 to Val at position 522 of the formula (1), wherein formula (1) is:

```
-32                                                 -23
Met—Thr—Ala—Pro—Gly—Ala—Ala—Gly—Arg—Cys—
                                                    -13
Pro—Pro—Thr—Thr—Trp—Leu—Gly—Ser—Leu—Leu—
                                                     -3
Leu—Leu—Val—Cys—Leu—Leu—Ala—Ser—Arg—Ser—
       1                                      8
Ile—Thr—Glu—Glu—Val—Ser—Glu—Tyr—Cys—Ser—
                                              18
His—Met—Ile—Gly—Ser—Gly—His—Leu—Gln—Ser—
                                              28
Leu—Gln—Arg—Leu—Ile—Asp—Ser—Gln—Met—Glu—
                                              38
Thr—Ser—Cys—Gln—Ile—Thr—Phe—Glu—Phe—Val—
                                              48
Asp—Gln—Glu—Gln—Leu—Lys—Asp—Pro—Val—Cys—
                                              58
Tyr—Leu—Lys—Lys—Ala—Phe—Leu—Leu—Val—Gln—
                                              68
X—Ile—Met—Glu—Asp—Thr—Met—Arg—Phe—Arg—
                                              78
Asp—Asn—Thr—Pro—Asn—Ala—Ile—Ala—Ile—Val—
                                              88
Gln—Leu—Gln—Glu—Leu—Ser—Leu—Arg—Leu—Lys—
                                              98
Ser—Cys—Phe—Thr—Lys—Asp—Tyr—Glu—Glu—His—
                                             108
Asp—Lys—Ala—Cys—Val—Arg—Thr—Phe—Tyr—Glu—
                                             118
Thr—Pro—Leu—Gln—Leu—Leu—Glu—Lys—Val—Lys—
                                             128
Asn—Val—Phe—Asn—Glu—Thr—Lys—Asn—Leu—Leu—
                                             138
Asp—Lys—Asp—Trp—Asn—Ile—Phe—Ser—Lys—Asn—
                                             148
Cys—Asn—Asn—Ser—Phe—Ala—Glu—Cys—Ser—Ser—
                                             158
Gln—Asp—Val—Val—Thr—Lys—Pro—Asp—Cys—Asn—
                                             168
Cys—Leu—Tyr—Pro—Lys—Ala—Ile—Pro—Ser—Ser—
                                             178
Asp—Pro—Ala—Ser—Val—Ser—Pro—His—Gln—Pro—
```

-continued

Leu—Ala—Pro—Ser—Met—Ala—Pro—Val—Ala—Gly— 188
Leu—Thr—Trp—Glu—Asp—Ser—Glu—Gly—Thr—Glu— 198
Gly—Ser—Ser—Leu—Leu—Pro—Gly—Glu—Gln—Pro— 208
Leu—His—Thr—Val—Asp—Pro—Gly—Ser—Ala—Lys— 218
Gln—Arg—Pro—Pro—Arg—Ser—Thr—Cys—Gln—Ser— 228
Phe—Glu—Pro—Pro—Glu—Thr—Pro—Val—Val—Lys— 238
Asp—Ser—Thr—Ile—Gly—Gly—Ser—Pro—Gln—Pro— 248
Arg—Pro—Ser—Val—Gly—Ala—Phe—Asn—Pro—Gly— 258
Met—Glu—Asp—Ile—Leu—Asp—Ser—Ala—Met—Gly— 268
Thr—Asn—Trp—Val—Pro—Glu—Glu—Ala—Ser—Gly— 278
Glu—Ala—Ser—Glu—Ile—Pro—Val—Pro—Gln—Gly— 288
Thr—Glu—Leu—Ser—Pro—Ser—Arg—Pro—Gly—Gly— 298
Gly—Ser—Met—Gln—Thr—Glu—Pro—Ala—Arg—Pro— 308
Ser—Asn—Phe—Leu—Ser—Ala—Ser—Ser—Pro—Leu— 318
Pro—Ala—Ser—Ala—Lys—Gly—Gln—Gln—Pro—Ala— 328
Asp—Val—Thr—Gly—Thr—Ala—Leu—Pro—Arg—Val— 338
Gly—Pro—Val—Arg—Pro—Thr—Gly—Gln—Asp—Trp— 348
Asn—His—Thr—Pro—Gln—Lys—Thr—Asp—His—Pro— 358
Ser—Ala—Leu—Leu—Arg—Asp—Pro—Pro—Glu—Pro— 368
Gly—Ser—Pro—Arg—Ile—Ser—Ser—Pro—Arg—Pro— 378
Gln—Gly—Leu—Ser—Asn—Pro—Ser—Thr—Leu—Ser— 388
Ala—Gln—Pro—Gln—Leu—Ser—Arg—Ser—His—Ser— 398
Ser—Gly—Ser—Val—Leu—Pro—Leu—Gly—Glu—Leu— 408
Glu—Gly—Arg—Arg—Ser—Thr—Arg—Asp—Arg—Arg— 418
Ser—Pro—Ala—Glu—Pro—Glu—Gly—Gly—Pro—Ala— 428
Ser—Glu—Gly—Ala—Ala—Arg—Pro—Leu—Pro—Arg— 438
Phe—Asn—Ser—Val—Pro—Leu—Thr—Asp—Thr—Gly— 448
His—Glu—Arg—Gln—Ser—Glu—Gly—Ser—Ser—Ser— 458
Pro—Gln—Leu—Gln—Glu—Ser—Val—Phe—His—Leu— 468
Leu—Val—Pro—Ser—Val—Ile—Leu—Val—Leu—Leu— 478
Ala—Val—Gly—Gly—Leu—Leu—Phe—Tyr—Arg—Trp— 488
Arg—Arg—Arg—Ser—His—Gln—Glu—Pro—Gln—Arg— 498
Ala—Asp—Ser—Pro—Leu—Glu—Gln—Pro—Glu—Gly— 508
Ser—Pro—Leu—Thr—Gln—Asp—Asp—Arg—Gln—Val— 518
Glu—Leu—Pro—Val 522 wherein x is Tyr or Asp.

2. The method of claim 1 wherein the macrophage-colony stimulating factor is a macrophage-colony stimulating factor having an amino acid primary sequence of Val at position 3 or Ser at position 4 to Thr at position 153 or an amino acid primary sequence of Val at position 3 or Ser at position 4 to Pro at position 214 of the formula (1).

3. The method of claim 1 wherein the macrophage-colony stimulating factor is a macrophage-colony stimulating factor having an amino acid primary sequence of Val at position 3 or Ser at position 4 to Thr at position 153 of the formula (1).

4. The method of claim 1 wherein the macrophage-colony stimulating factor is a macrophage-colony stimulating factor having an amino acid primary sequence of Val at position 3 or Ser at position 4 to Pro at position 214 of the formula (1).

5. The method of claim 1 wherein the macrophage-colony stimulating factor is a macrophage-colony stimulating factor having an amino acid primary sequence of Val at position 3 to Thr at position 153 of the formula (1).

6. The method of claim 1, wherein the allergy is Type I allergy.

7. The method of claim 1, wherein the allergy is Type IV allergy.

8. The method of claim 1, wherein the macrophage-colony stimulating factor is a macrophage-colony stimulating factor having a amino acid primary sequence of Met at position -32 to Val at position 522 of the formula (1).

* * * * *